United States Patent
Wang et al.

(10) Patent No.: US 11,382,574 B2
(45) Date of Patent: Jul. 12, 2022

(54) STATIONARY IN-VIVO GRATING-ENABLED MICRO-CT ARCHITECTURE (SIGMA)

(71) Applicant: RENSSELAER POLYTECHNIC INSTITUTE, Troy, NY (US)

(72) Inventors: Ge Wang, Loudonville, NY (US); Wenxiang Cong, Albany, NY (US); Qingsong Yang, Troy, NY (US); Guang Li, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 16/761,543

(22) PCT Filed: Nov. 6, 2018

(86) PCT No.: PCT/US2018/059366
§ 371 (c)(1),
(2) Date: May 5, 2020

(87) PCT Pub. No.: WO2019/090299
PCT Pub. Date: May 9, 2019

(65) Prior Publication Data
US 2020/0261030 A1  Aug. 20, 2020

Related U.S. Application Data

(60) Provisional application No. 62/581,991, filed on Nov. 6, 2017.

(51) Int. Cl.
*A61B 6/03* (2006.01)
*A61B 6/00* (2006.01)
*G01N 23/041* (2018.01)

(52) U.S. Cl.
CPC ............ *A61B 6/032* (2013.01); *A61B 6/4014* (2013.01); *A61B 6/4291* (2013.01); *A61B 6/484* (2013.01); *G01N 23/041* (2018.02)

(58) Field of Classification Search
CPC ..... A61B 6/032; A61B 6/4014; A61B 6/4291; G01N 23/041
See application file for complete search history.

(56) References Cited

U.S. PATENT DOCUMENTS

| 4,916,718 A | 4/1990 | Manring |
| 5,402,460 A * | 3/1995 | Johnson ............... G01N 23/046 378/10 |

(Continued)

FOREIGN PATENT DOCUMENTS

| CN | 102014755 A | 4/2011 |
| CN | 105580054 A | 5/2016 |

(Continued)

OTHER PUBLICATIONS

International Search Report and The Written Opinion of the International Searching Authority, International Application Mo. PCT/US2018/059366, dated Jan. 22, 2019.

*Primary Examiner* — Chih-Cheng Kao
(74) *Attorney, Agent, or Firm* — Murtha Cullina LLP; Anthony P. Gangemi

(57) ABSTRACT

A stationary in-vivo grating-enabled micro-CT (computed tomography) architecture (SIGMA) system includes CT scanner control circuitry and a number of imaging chains. Each imaging chain includes an x-ray source array, a phase grating, an analyzer grating and a detector array. Each imaging chain is stationary and each x-ray source array includes a plurality of x-ray source elements. Each imaging chain has a centerline, the centerlines of the number of imaging chains intersect at a center point and a first angle between the centerlines of a first adjacent pair of imaging chains equals a second angle between the centerlines of a second adjacent pair of imaging chains. A plurality of selected x-ray source elements of a first x-ray source array (Continued)

is configured to emit a plurality of x-ray beams in a multiplexing fashion.

22 Claims, 11 Drawing Sheets

(56) References Cited

U.S. PATENT DOCUMENTS

| | | | |
|---|---|---|---|
| 5,982,845 A | 11/1999 | Sidoti et al. | |
| 7,693,256 B2 | 4/2010 | Brahme et al. | |
| 7,835,486 B2 | 11/2010 | Basu et al. | |
| 9,478,049 B2 | 10/2016 | Bippus et al. | |
| 9,757,081 B2 | 9/2017 | Proksa | |
| 2007/0183583 A1* | 8/2007 | Baumann | A61B 6/4233 378/145 |
| 2007/0206726 A1* | 9/2007 | Lu | G01N 23/203 378/146 |
| 2009/0003514 A1 | 1/2009 | Edic et al. | |
| 2009/0022264 A1 | 1/2009 | Zhou et al. | |
| 2009/0196393 A1* | 8/2009 | Wang | A61B 6/508 378/4 |
| 2010/0072376 A1 | 3/2010 | Ronda | |
| 2010/0080342 A1 | 4/2010 | Takahashi | |
| 2011/0180715 A1 | 7/2011 | Ronda et al. | |
| 2012/0301004 A1* | 11/2012 | Kingston | A61B 6/032 382/131 |
| 2013/0266115 A1 | 10/2013 | Fan et al. | |
| 2015/0001398 A1 | 1/2015 | Ronda et al. | |
| 2016/0135769 A1 | 5/2016 | Wang et al. | |
| 2016/0242726 A1 | 8/2016 | Koehler et al. | |
| 2017/0186194 A1 | 6/2017 | Koehler et al. | |

FOREIGN PATENT DOCUMENTS

| | | |
|---|---|---|
| CN | 206021742 U | 3/2017 |
| CN | 107424890 A | 12/2017 |
| CN | 107452583 A | 12/2017 |
| CN | 108310681 A | 7/2018 |
| CN | 108366773 A | 8/2018 |
| DE | 19845756 A1 | 4/2000 |
| EP | 3102109 B1 | 12/2015 |
| FR | 2834179 A1 | 6/2003 |
| FR | 2839894 A1 | 5/2021 |
| JP | 2006500145 A | 1/2006 |
| JP | 2008538966 A | 11/2008 |
| JP | 2011503570 A | 1/2011 |
| JP | 6014323 B2 | 9/2016 |
| JP | 201764240 A | 4/2017 |
| JP | 2017205326 A | 11/2017 |
| RU | 2575392 C2 | 2/2010 |
| WO | 2013171657 A1 | 11/2013 |
| WO | 2015014677 A1 | 2/2015 |
| WO | 2018104132 A1 | 6/2018 |

* cited by examiner

200

508

STATIONARY IN-VIVO GRATING-ENABLED MICRO-CT ARCHITECTURE (SIGMA)

CROSS REFERENCE TO RELATED APPLICATION(S)

This application claims the benefit of U.S. Provisional Application No. 62/581,991, filed Nov. 6, 2017, which is incorporated by reference as if disclosed herein in its entirety.

FIELD

The present disclosure relates to a micro-CT (computed tomography) architecture, in particular to, a stationary in-vivo grating-enabled micro-CT architecture.

BACKGROUND

Cancer commonly metastasizes in bone, which results in pain, pathological fracture, neurologic impairment, decreased quality of life, and is a significant contributor to mortality. Bone tumors often occur in the vertebra, and also pelvis, femur, ribs, and skull. Imaging of bone metastasis is invaluable for its detection, diagnosis, prognostication, treatment, and follow-up. While an ideal model does not exist, preclinical research has been extensive with small animal models of tumor invasion and skeletal metastases, relevant to mammary and prostate cancer as well as other types of carcinoma. In the clinical and preclinical settings, neither x-ray radiography nor CT is sensitive for early detection of bone lesions. Nuclear imaging and MRI are valuable but not specific.

SUMMARY

In some embodiments, an apparatus for stationary in-vivo grating-enabled micro-CT (computed tomographic) imaging includes a number of imaging chains. Each imaging chain includes an x-ray source array, a phase grating, an analyzer grating and a detector array. Each each imaging chain is stationary and each x-ray source array includes a plurality of x-ray source elements. Each imaging chain has a centerline. The centerlines of the number of imaging chains intersect at a center point and a first angle between the centerlines of a first adjacent pair of imaging chains equals a second angle between the centerlines of a second adjacent pair of imaging chains. A plurality of selected x-ray source elements of a first x-ray source array is configured to emit a plurality of x-ray beams in a multiplexing fashion.

In some embodiments of the apparatus, each x-ray source array of a plurality of x-ray source arrays is configured to emit a respective x-ray beam at a same time. In some embodiments of the apparatus, the number of imaging chains is three, each imaging chain is configured to provide tri-contrasts comprising attenuation, phase shift and small angle scattering and each x-ray source array and each detector array are planar or curved. In some embodiments, each of the plurality of x-ray source elements is individually digitally addressable. In some embodiments, each x-ray source element has a spot size in the range of 5 µm (micrometers) to 20 µm. In some embodiments, the imaging chains have a resolution on the order of 30 µm (micrometers).

In some embodiments, a stationary in-vivo grating-enabled micro-CT (computed tomography) architecture (SIGMA) system includes CT scanner control circuitry and a number of imaging chains. Each imaging chain includes an x-ray source array, a phase grating, an analyzer grating and a detector array. Each imaging chain is stationary and each x-ray source array includes a plurality of x-ray source elements. Each imaging chain has a centerline. The centerlines of the number of imaging chains intersect at a center point and a first angle between the centerlines of a first adjacent pair of imaging chains equals a second angle between the centerlines of a second adjacent pair of imaging chains. A plurality of selected x-ray source elements of a first x-ray source array is configured to emit a plurality of x-ray beams in a multiplexing fashion.

In some embodiments of the SIGMA system, each x-ray source array of a plurality of x-ray source arrays is configured to emit a respective x-ray beam at a same time. In some embodiments of the SIGMA system, the number of imaging chains is three, each imaging chain is configured to provide tri-contrasts comprising attenuation, phase shift and small angle scattering and each x-ray source array and each detector array are planar or curved. In some embodiments, each of the plurality of x-ray source elements is individually digitally addressable. In some embodiments, each x-ray source element has a spot size in the range of 5 µm (micrometers) to 20 µm. In some embodiments, the imaging chains have a resolution on the order of 30 µm (micrometers). In some embodiments of the SIGMA system, the CT scanner control circuitry is configured to reconstruct a micro-CT image utilizing on the order of 100 projections.

In some embodiments, a method for in-vivo grating-enabled micro-CT (computed tomography) imaging includes providing a number of imaging chains. Each imaging chain includes an x-ray source array, a phase grating, an analyzer grating and a detector array. Each imaging chain is stationary and each x-ray source array includes a plurality of x-ray source elements. Each imaging chain has a centerline. The centerlines of the number of imaging chains intersect at a center point and a first angle between the centerlines of a first adjacent pair of imaging chains equals a second angle between the centerlines of a second adjacent pair of imaging chains. The method further includes emitting, by a plurality of selected x-ray source elements of a first x-ray source array, plurality of x-ray beams in a multiplexing fashion.

In some embodiments, the method includes emitting, by each x-ray source array of a plurality of x-ray source arrays, a respective x-ray beam at the same time. In some embodiments, the method includes providing, by each imaging chain, tri-contrasts comprising attenuation, phase shift and small angle scattering, the number of imaging chains is three and each x-ray source array and each detector array are planar or curved. In some embodiments of the method, each of the plurality of x-ray source elements is individually digitally addressable. In some embodiments of the method, each x-ray source element has a spot size in the range of 5 µm (micrometers) to 20 µm. In some embodiments of the method, the imaging chains have a resolution on the order of 30 µm (micrometers).

In some embodiments of the method, the method may further include, reconstructing, by a CT scanner control circuitry, a micro-CT image utilizing on the order of 100 projections.

BRIEF DESCRIPTION OF THE DRAWINGS

The drawings show embodiments of the disclosed subject matter for the purpose of illustrating features and advantages of the disclosed subject matter. However, it should be understood that the present application is not limited to the precise arrangements and instrumentalities shown in the drawings, wherein.

DETAILED DESCRIPTION

Figure 1:
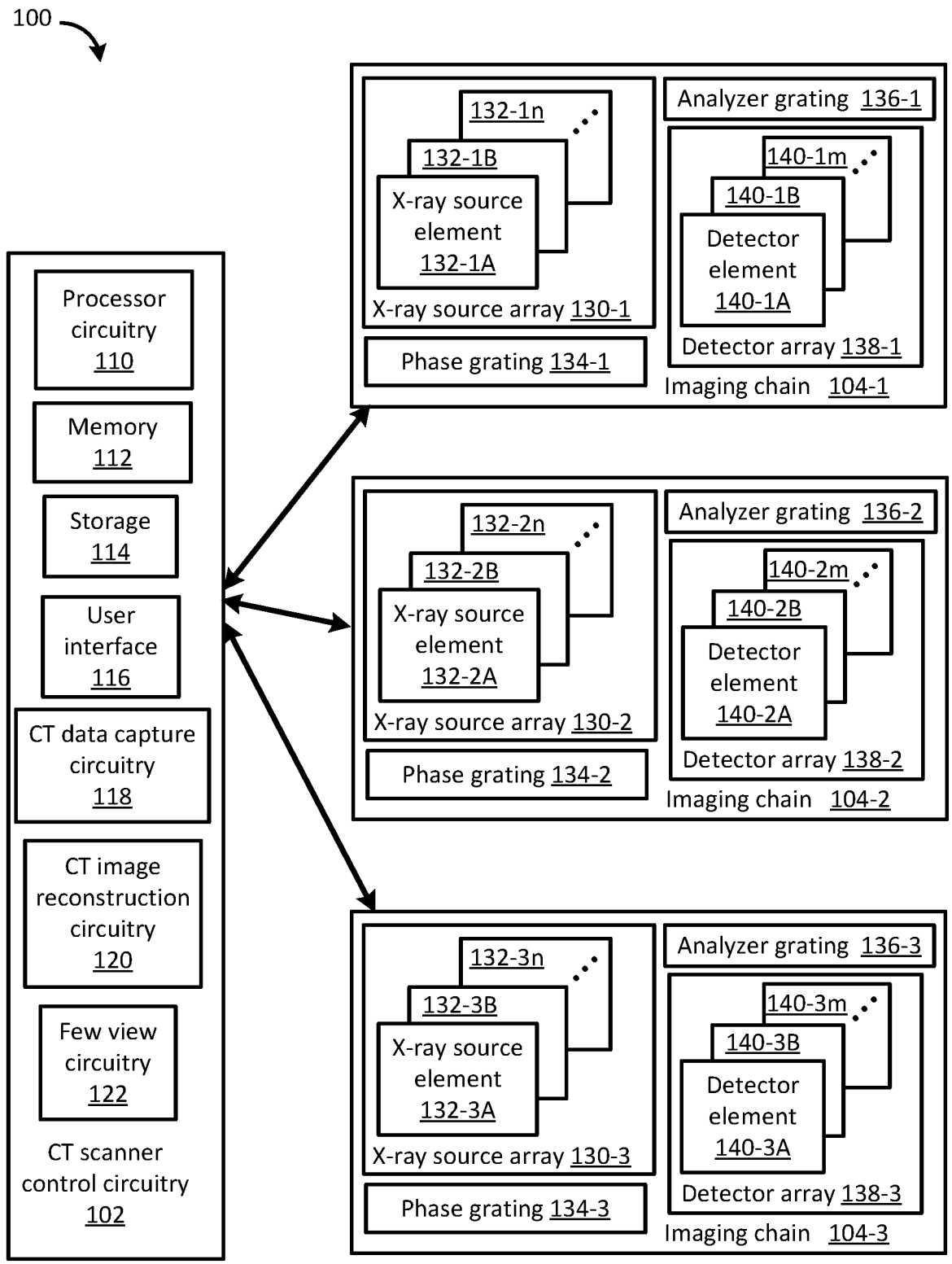
FIG. 1 illustrates a functional block diagram of a stationary in-vivo grating-enabled micro-CT architecture (SIGMA) system according to several embodiments of the present disclosure.

X-ray CT remains a primary imaging modality but current CT/micro-CT suffers from insufficient biological contrast. In recent years, x-ray grating-based imaging in tri-contrasts (attenuation, phase shift, and small angle scattering) has been under development. This grating-enabled technique has advantages over conventional micro-CT/CT: vasculature, normal and cancerous tissues have much higher refractive coefficients than the attenuation counterpart; and small angle scattering contrast reveals rich signatures on micron-/nanoscales for micro-morphological classification. Bone architecture, mineralization, and organic matrix quality determine bone fracture resistance which deteriorates with bone metastases.

A conventional micro-CT scanner is configured to provide attenuation-based images. An x-ray grating-enabled micro-CT scanner is configured to obtain x-ray phase contrast and small angle scattering (also referred to as dark field) contrast simultaneously with conventional linear attenuation information. X-ray tri-contrast imaging, enabled by micro-fabricated x-ray gratings, has outstanding capabilities for comprehensive and quantitative 3D pathology of tissues including bone ex vivo and in vivo, more informative than x-ray attenuation imaging alone.

Historically, x-ray interferometric imaging was performed with a relatively expensive synchrotron radiation facility. Currently, x-ray grating-enabled interferometric imaging in the Talbot or Talbot-Lau mode can be implemented in a lab setting with a regular or microfocus x-ray tube, offering two more contrast mechanisms than conventional micro-CT/CT. These additional contrast mechanisms are configured to produce phase contrast and dark field signals. Phase contrast and dark field signals may be useful for imaging biological features such as tumors, vasculature, microcalcification, bone mineral characteristics, protein crosslinking, and bone architecture. In preclinical applications, x-ray grating-based imaging permits finer resolution at less cost than micro-PET/SPECT and micro-MRI while providing relatively rich biological tissue information competitive with that from nuclear imaging and MRI Compared with optical/fluorescence and ultrasound imaging, x-ray grating-based imaging enjoys deeper penetration at higher quantitative accuracy.

Talbot-Lau interferometers typically use three one dimensional (1D) gratings: a source grating (G0) with micron-sized openings placed near an ordinary x-ray source to produce a periodic array of sourcelets, a phase grating (G1) to produce interference fringes at Talbot distances when illuminated with the x-ray beamlets from G0, and a detector (i.e., analyzer) grating (G2) to analyze the Talbot fringes. With a micro-focus x-ray tube, G0 is not needed, the Talbot fringes can be formed with G1 only. In this case, a Talbot-Lau interferometer is reduced to a Talbot interferometer. With either interferometric setup, placement of an object in the x-ray path distorts the interference fringes. To quantify the distortion with a regular x-ray detector array, the fringes are analyzed via so-called "phase-stepping"; for example, recording detected x-ray projections as G2 is stepwise displaced perpendicular to the grating lines. Two challenges of Talbot-Lau or Talbot interferometry are: (1) relatively difficult grating alignment and (2) relatively time-consuming data collection. For example, alignment of each x-ray grating includes micron-level accuracy in five degrees of freedom (x, y, z, and two angular variables). This process is rather challenging and relatively tedious especially within a rotating micro-CT gantry. For each of a relatively large number of viewing angles multiple phase-stepping operations are performed. The total data acquisition time is longer than that with conventional micro-CT. Thus, conventional Talbot or Talbot-Lau interferometry may suffer from relatively low throughput, compromised image quality and little practicality for in vivo preclinical studies.

Current micro-CT systems follow the conventional CT architecture, in which an x-ray tube and an associated detector array are continuously rotated. For x-ray grating-based micro-CT, the mechanical rotation and instability results in a tolerance that is greater than a desired micron-level tolerance. Historically, carbon nanotubes (CNT) sources were configured for stationary micro-CT (attenuation contrast only), with inadequate image quality due to its suboptimal half-scan architecture and reconstruction algorithm.

For in-vivo characterization of bone matrix quality in tumor, osteoporosis, osteoarthritis (OA) and T2D (Type 2 diabetes), plain radiography, CT, and MRI provide anatomical information, while PET, SPECT, and skeletal scintigraphy (SS) depict metabolic activities for monitoring the development of metastatic bone tumors. There is no gold standard imaging technique, and the current consensus is to use multimodality imaging for improved sensitivity and specificity. However, image biomarkers have been rather limited on cancer-induced changes in bone properties, which are major determinants of fracture risk.

Generally, this disclosure relates to a stationary in-vivo grating-enabled micro-CT (computed tomography) architecture (SIGMA) system. An apparatus, method and/or system are configured to replace mechanical x-ray source rotation (i.e., gantry rotation) with electronic multiplexing facilitating x-ray interferometry by providing micron-level alignment. The apparatus, method and/or system includes three stationary imaging chains that may be operated in parallel. Each imaging chain includes x-ray gratings (phase grating, analyzer grating), an x-ray source array and a detector arrays. Each x-ray source array includes a plurality of x-ray source elements that may be selected electronically and operated individually. Each x-ray source element may be configured to provide an x-ray spot of a defined size corresponding to an x-ray beam configured to encounter an object to be imaged. The apparatus, method and/or system may be further configured to include few-view image reconstruction, as will be described in more detail below.

In an embodiment, the SIGMA system includes three imaging chains that may be used in parallel, thus tripling the imaging speed. Each imaging chain may thus include an x-ray source array, a phase grating, an analyzer grating and a detector array. The source arrays may be symmetrically arranged along with the corresponding detector array and phase and analyzing gratings between the source and detector. Each imaging chain may be configured to perform a limited-angle scan via electronic manipulation of x-ray focal spots.

The SIGMA system may be configured with two non-overlapped regions on each detector array that are used for data collection in parallel. Two x-ray spots in each source array are turned on to cast two nonoverlapped projections on the corresponding detector array. The data acquisition efficiency may then be doubled. The few view reconstruction technique is configured to reduce the number of projections by several folds. Thus, the SIGMA system may scan an object an order of magnitude faster than the existing systems without compromising image quality.

Tri-contrast images may be reconstructed from data collected over three limited-angular ranges in a compressed sensing framework providing 30 μm resolution and 30-minute scan time, and characterized in phantom experiments at an x-ray dose level comparable to that of a typical micro-CT scan. Thus, the SIGMA system is configured to provide stable imaging performance at a resolution on the order of 30 μm (micrometers) in x-ray tri-contrasts (i.e., attenuation, phase shift, small angle scattering). The SIGMA system is further configured to provide a scan time of on the order of 30 minutes.

In some embodiments, a stationary in-vivo grating-enabled micro-CT (computed tomography) architecture (SIGMA) system includes CT scanner control circuitry and a number of imaging chains. Each imaging chain includes an x-ray source array, a phase grating, an analyzer grating and a detector array. Each imaging chain is stationary and each x-ray source array includes a plurality of x-ray source elements. Each imaging chain has a centerline. The centerlines of the number of imaging chains intersect at a center point and a first angle between the centerlines of a first adjacent pair of imaging chains equals a second angle between the centerlines of a second adjacent pair of imaging chains. A plurality of selected x-ray source elements of a first x-ray source array is configured to emit a plurality of x-ray beams in a multiplexing fashion.

FIG. 1 illustrates a functional block diagram of a stationary in-vivo grating-enabled micro-CT architecture (SIGMA) system 100 according to several embodiments of the present disclosure. System 100 includes CT scanner control circuitry 102 and a plurality of imaging chains 104-1, 104-2, 104-3. CT scanner control circuitry 102 is configured to manage operation of SIGMA system 100 including, but not limited to, providing control signals to and capturing CT data from imaging chains 104-1, 104-2, 104-3. CT scanner control circuitry 102 is further configured to manage reconstructing a CT image based, at least in part, on the captured CT data. The captured CT data is related to linear attenuation contrast, phase shift and small angle scattering (i.e., dark field), as will be described in more detail below.

CT scanner control circuitry 102 includes processor circuitry 110, memory 112, storage 114, user interface 116, CT data capture circuitry 118, CT image reconstruction circuitry 120 and few view circuitry 122. Processor circuitry 110 may include, but is not limited to, a single core processing unit, a multicore processor, one graphics processing unit (GPU), a plurality of GPUs, a microcontroller, an application-specific integrated circuit (ASIC), a field programmable gate array (FPGA), a programmable logic device (PLD), etc. Processor circuitry 110 may be configured to perform operations of CT scanner control circuitry 102. Memory 112 and/or storage 114 may be configured to store information and/or data associated with operation of CT scanner control circuitry 102. User interface 116 may include a user input device (e.g., keyboard, keypad, mouse, touchpad, etc.) and/or a user output device (e.g., a display).

Each imaging chain includes an x-ray source array, a phase grating, an analyzer grating and a detector array. Each x-ray source array includes a plurality of x-ray source elements and each detector array includes a plurality of detector elements. Thus, a first imaging chain 104-1 includes x-ray source array 130-1, phase grating 134-1, analyzer grating 136-1 and detector array 138-1. X-ray source array 130-1 includes a plurality of x-ray source elements 132-1A, 132-1B, . . . , 132-1$n$ and detector array 138-1 includes a plurality of detector elements 140-1A, 140-1B, . . . 140-1$m$. Similarly, a second imaging chain 104-2 includes x-ray source array 130-2, phase grating 134-2, analyzer grating 136-2 and detector array 138-2. X-ray source array 130-2 includes a plurality of x-ray source elements 132-2A, 132-2B, . . . , 132-2$n$ and detector array 138-2 includes a plurality of detector elements 140-2A, 140-2B, . . . 140-2$m$. A third imaging chain 104-3 includes x-ray source array 130-3, phase grating 134-3, analyzer grating 136-3 and detector array 138-3. X-ray source array 130-3 includes a plurality of x-ray source elements 132-3A, 132-3B, . . . , 132-3$n$ and detector array 138-3 includes a plurality of detector elements 140-3A, 140-3B, . . . 140-3$m$.

As used herein, for ease of description, "imaging chain 104" without "-x" (x=1, 2 or 3) refers to any of imaging chains 104-1, 104-2, 104-3. Similarly, "x-ray source array 130" refers to any of x-ray source arrays 130-1, 130-2, 130-3; "phase grating 134" refers to any of phase gratings 134-1, 134-2, 134-3; "analyzer grating 136" refers to any of analyzer gratings 136-1, 136-2, 136-3 and "detector array 138" refers to any of detector arrays 138-1, 138-2, 138-3. Thus, imaging chain 104 may include x-ray source array 130, phase grating 134, analyzer grating 136 and detector array 138. Phase grating 134 corresponds to grating G1 and analyzer grating 136 corresponds to grating G2 in the Talbot-Lau interferometric framework.

In an embodiment, the x-ray source elements of each x-ray source array may be digitally addressable. Thus, each x-ray source element may be individually controlled by, e.g., CT data capture circuitry 118. In one nonlimiting example, the x-ray source arrays may correspond to a digitally addressable x-ray source (DAXS) technology available from Stellarray. In another non-limiting example, each x-ray source element may correspond to a microfocus tube available from Hamamatsu (e.g., the Hamamatsu L10101 microfocus tube). For example, the x-ray tube may be operable with output power from 4-20 W (watts) on spot size from 5-20 µm (micrometer). Thus, each x-ray source array may correspond to an array of these microfocus tubes. In an embodiment, each x-ray source element may be configured with up to 3 times more output power on each x-ray spot compared to the Hamamatsu microfocus tube and may be configured to have relatively simpler cooling, and multiplexing mechanisms for a relatively fast imaging speed.

Figure 2A:
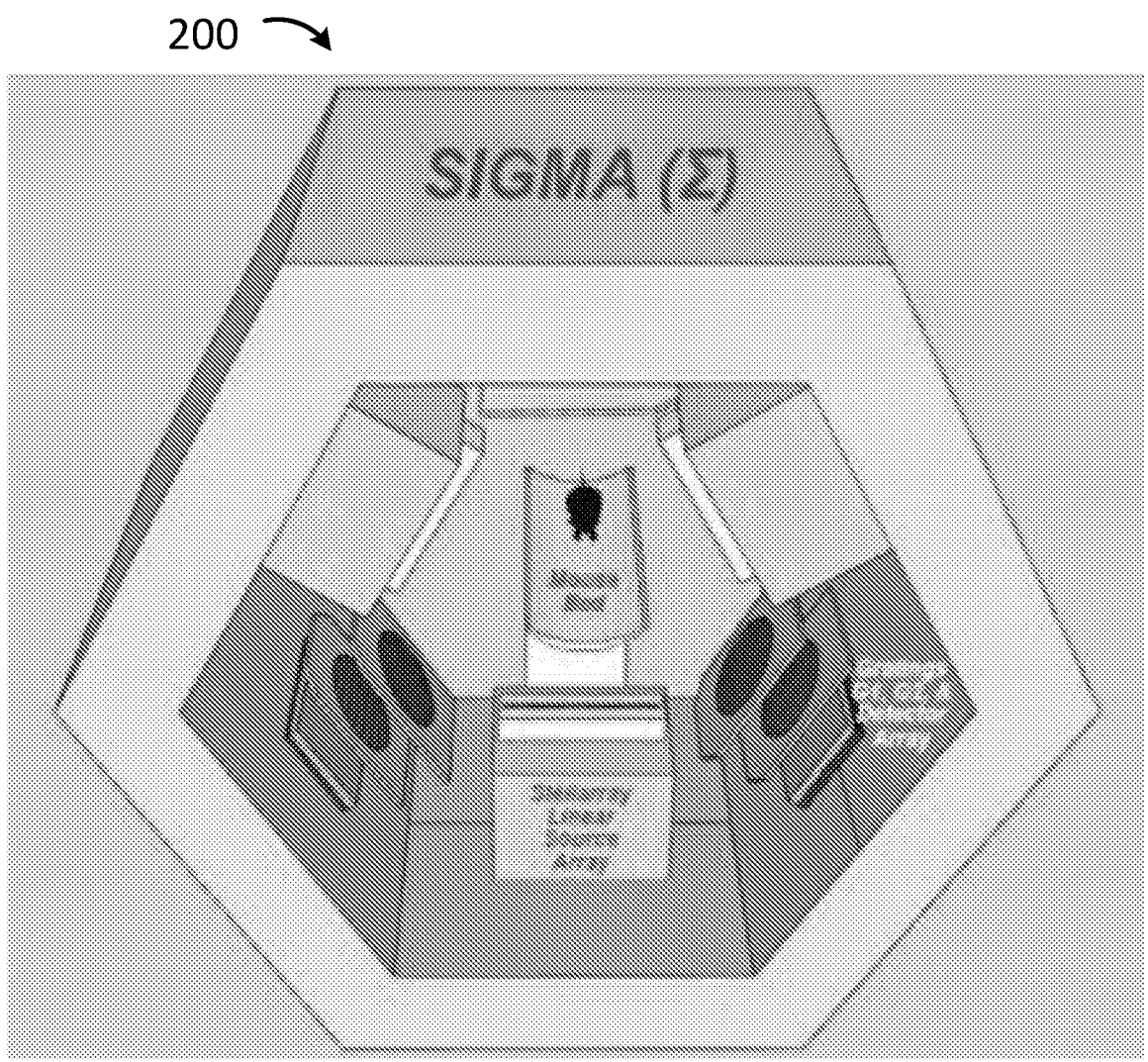
FIGS. 2A and 2B are an artist rendition and a line drawing of a SIGMA system, respectively, according to an embodiment of the present disclosure.
Figure 2B:
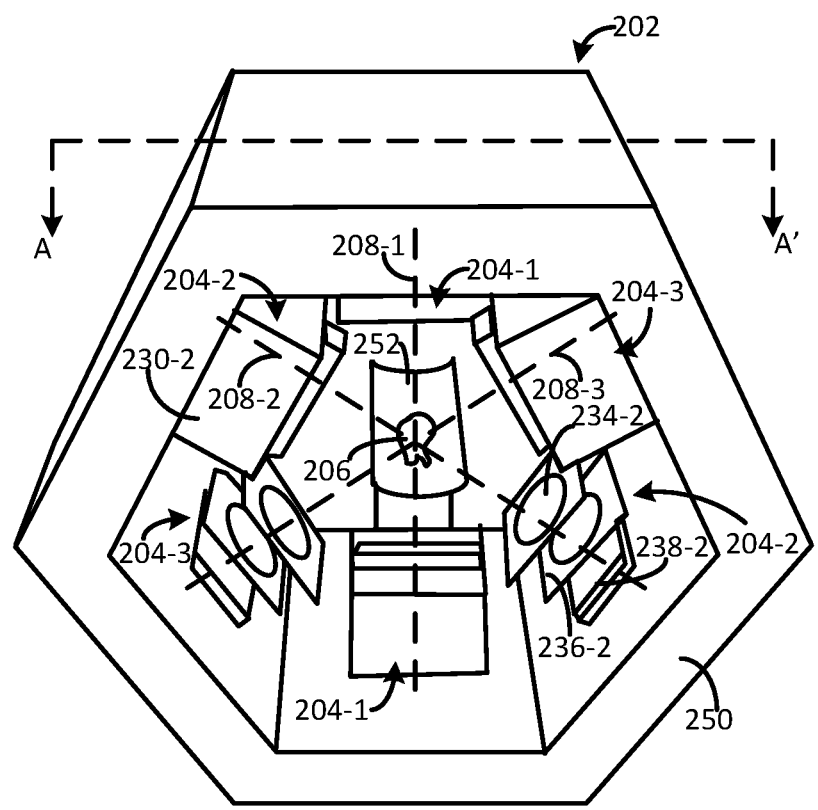

FIGS. 2A and 2B are an artist rendition 200 and a line drawing 202 of a SIGMA system, respectively, according to an embodiment of the present disclosure. The artist rendition 200 and line drawing 202 are meant to illustrate the relative positions of the x-ray chains and object to be imaged, as described herein. The respective positions of the x-ray chains and object to be imaged are fixed, i.e., are stationary. In the SIGMA system 200, 202, scanning is provided by selectively operating a plurality (e.g., a sequence) of x-ray source elements to emit x-ray beams and detecting corresponding received x-ray beams.

Turning to FIG. 2B, SIGMA system 202 includes three imaging chains 204-1, 204-2, and 204-3. Each imaging chain, e.g., imaging chain 204-2, includes an x-ray source array 230-2, a phase grating 234-2, an analyzer grating 236-2 and a detector array 238-2. FIG. 2B further includes an object to be imaged 206. The object to be imaged 206 is centered relative to the imaging chains 204-1, 204-2, 204-3 that are spaced (relatively positioned) at equal angles. Each imaging chain has a centerline. The centerlines of the imaging chains intersect at the center point and a first angle between the centerlines of a first adjacent pair of imaging chains equals a second angle between the centerlines of a second adjacent pair of imaging chains. In other words, an imaging chain centerline, e.g., centerline 208-1, extending from a center of an emitting surface of the x-ray source array to a center of facing surfaces of the corresponding phase grating, analyzer grating and detector array may form an angle of 60 degrees from each other imaging chain centerline 208-2, 208-3. The object to be imaged 206 may be positioned at an intersection of the imaging chain centerlines. The intersection of the imaging chain centerlines corresponds to a center point.

The phase grating (i.e., G1) and analyzer grating (i.e., G2) of each imaging chain correspond to a Talbot interferometer. The SIGMA system 202 includes a mechanical frame 250 and a horizontal mouse bed 252 with physiological supporting/gating apparatus, all of which are on a base optical bench. The x-ray interferometric imaging chains 204-1, 204-2, 204-3 are symmetrically arranged around the mouse bed 252 (and object to be imaged 206), forming a generally hexagonal configuration. Each x-ray interferometer (i.e., imaging chain) includes a linear x-ray source array, a phase grating, an analyzer grating, and a flat panel detector array. The Talbot distance may be computed for a p-shifting phase grating. The selection of the Talbot mode is configured to avoid a possibly long and costly G0 grating (i.e., Talbot-Lau interferometry), simplify the system alignment process and help improve image resolution with the fine focal spot.

Figure 2C:
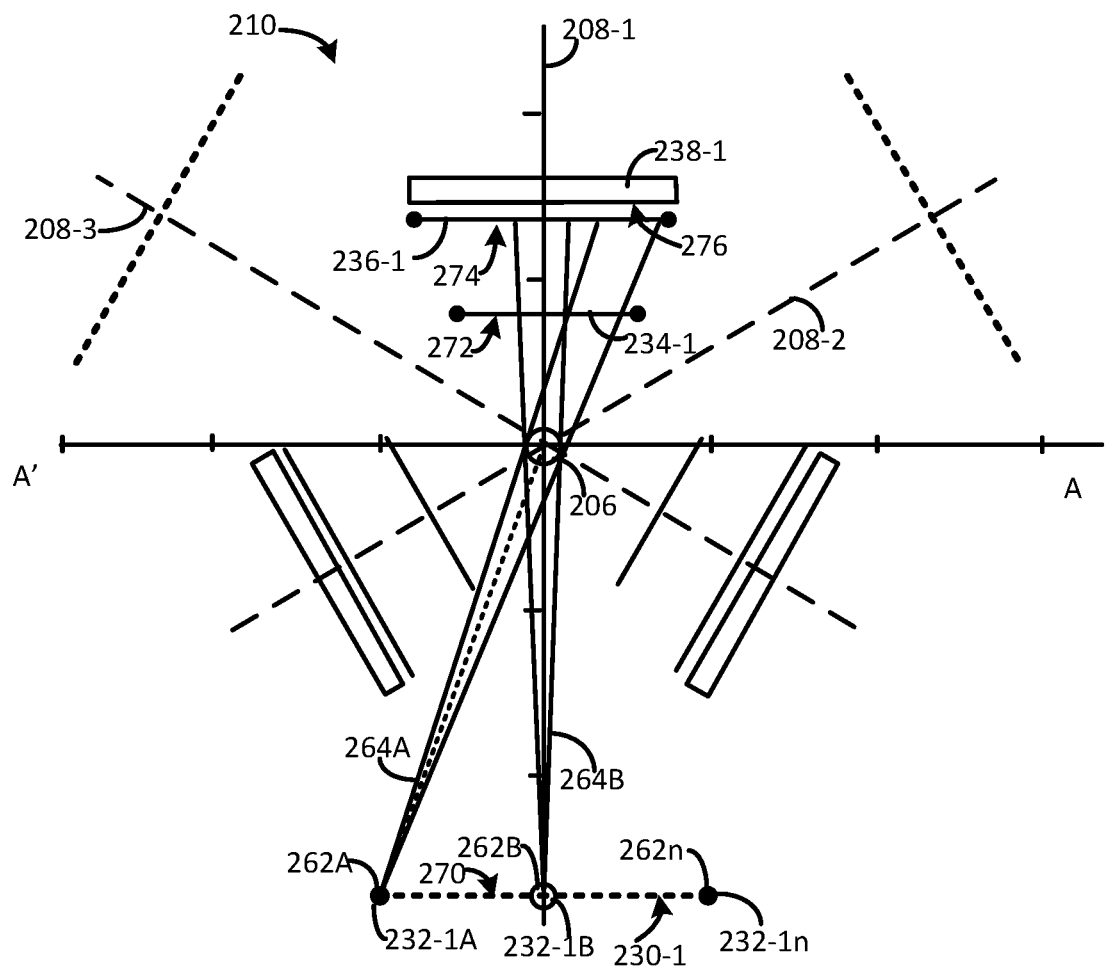
FIG. 2C is a section view (A-A') of the SIGMA system of FIG. 2B illustrating imaging geometry for the SIGMA system of FIGS. 2A and 2B.

FIG. 2C is a section view (A-A') 210 of the SIGMA system 202 of FIG. 2B. Section view 210 is configured to illustrate the imaging geometry for the SIGMA system of FIGS. 2A and 2B. The first imaging chain 204-1 includes x-ray source array 230-1, phase grating 234-1, analyzer grating 236-1 and detector array 238-1. X-ray source array 230-1 includes a plurality of x-ray source elements, e.g., 232-1A, 232-1B, . . . , 232-1n, and detector array 238-1 includes a plurality of detector elements (not shown).

The x-ray source array 230-1, phase grating 234-1, analyzer grating 236-1 and detector array 238-1 are generally rectangular. An emission surface 270 of the x-ray source array 230-1 is planar or curved and is configured to face respective incident surfaces 272, 274, 276 of the phase grating 234-1, analyzer grating 236-1 and detector array 238-1. The incident surface 276 of the detector array is planar or curved. As used herein, "planar" means planar to within manufacturing tolerances and including apertures (if any) that may be defined in the surface to accommodate x-ray source elements or detector elements. As used herein, "curved" means curved to within manufacturing tolerances and including apertures (if any) that may be defined in the surface to accommodate x-ray source elements or detector elements. Thus, each x-ray source array and each detector array are planar or curved. The centerline 208-1 of the imaging chain 204-1 is generally perpendicular to the surfaces 270, 272, 274, 276 and is positioned generally at the center of each surface. The centerline 208-1 passes through the object to be imaged 206.

Each x-ray source element may correspond to a respective x-ray spot. Thus, x-ray source element 232-1A corresponds to x-ray spot 262A, x-ray source element 232-1B corresponds to x-ray spot 262B, etc. The x-ray spots may be electronically multiplexed. In other words, one or more x-ray source elements may be selected and configured to emit x-ray beam(s) at a point in time. At a later point in time, one or more other x-ray source elements may then be selected and configured to emit x-ray beam(s). A plurality of selected x-ray source elements may be configured to emit respective x-ray beams in parallel. Thus, a plurality of selected x-ray source elements of an x-ray source array may be configured to emit a plurality of x-ray beams in a multiplexing fashion. The electronic multiplexing is configured to replace physical rotation of the gantry of a conventional CT imaging system. For example, each x-ray source array, e.g., x-ray source array 230-1, may be configured to generate 40 projection views (i.e., 40 sequential selections of one or more x-ray source elements) and to support a field of view of 25 mm. Although each of the three imaging chains covers a limited angular range, the three continuous angular segments are evenly distributed over a full-scan range, representing a relatively stable fashion compared to a conventional limited-angle tomographic setting.

Alternatively or additionally to the source-level parallelism, an area of each detector can be used in parallel. For example, each line x-ray source array can be multiplexed to emit two collimated x-ray beams at the same time, e.g., x-ray beam 264A and x-ray beam 264B. Initially, the left-most source spot 262A (corresponding to x-ray source element 232-1A) and the middle source spot 262B (corresponding to x-ray source element 232-1B) can be turned on. These two beams 264A, 264B do not interact with each other on the G2 grating 236-1 and the detector 238-1 surface 276. Then, the emitting points (i.e., selected x-ray source elements) can be stepwise shifted rightward (in the figure) until the right-most source spot 262n (corresponding to x-ray source element 232-1n) is fired. Thus, the scan time may be cut by half compared to providing a single x-ray beam at a sequence of points in time.

In one nonlimiting example, each x-ray source array, e.g., x-ray source array 230-1, may include a plurality of 50 µm x-ray source elements. In another example, each x-ray source array may include a plurality of 5 µm source elements. In operation, the SIGMA system may be calibrated to ensure the three imaging chains are co-registered. A precision phantom with small fiducial markers may be used to localize the imaging center for the three pairs of the source and detector arrays. For the gratings alignments, the analyzer grating G2 may be slightly rotated until the Moiré fringe on the detector exhibits a vertical orientation. The phase grating G1 may be slightly rotated to reach a uniform intensity image on the detector. Then, the relative distances of the gratings may be fine-tuned to minimize the Moiré fringes. Locally linear embedding methods may then be used to further refine the parameters of the imaging geometry from collected data.

The SIGMA system is configured to maintain the mouse bed (and thus the object to be imaged) and gratings (phase and analyzer) fixed (i.e., stationary) during data acquisition thus providing a relatively robust imaging system performance. Physiological gating for tri-contrast datasets may be introduced for improved spatial and temporal resolution. In an embodiment, interior tomography may be implemented to focus on a region of interest (ROI) inside an animal. Arrays of pre-source collimators may be utilized for global and interior imaging modes, respectively.

Table 1 contains system parameters and performance indices for one example SIGMA system according to the present disclosure.

TABLE 1

| Components | |
|---|---|
| Three x-ray source arrays | Voltage: up to 100 kV |
| | Current: up to 1 mA |
| | Focal Spot Size: 5/50 μm |
| | Output Power: 4-20 W |
| Grating G1 (phase grating) | 4 μm, 101.6 mm × 40 mm Area |
| Grating G2 (analyzer grating) | 2.32 μm, 150 mm × 60 mm Area |
| Detector array | CMOS Flat Panel |
| Geometric Parameters (for Global/Interior Scans) | |
| Source Length/Pitch/Energy | 200 mm/5 mm/40 keV |
| G1-to-Source array Distance | 350 mm (Depending on x-ray energy, grating period) |
| G1-to-G2 Distance | 56.2 mm |
| Detector Length/Pitch | 150 mm/50 μm |
| Performance Indices | |
| Image Quality | 30 μm @ 5% MTF |
| Scan Time per Mouse | <30 min. (40 s per view) |
| Processing & Recon. Time | <5 min. |
| Radiation Dose | <10 mSv per scan |

Figure 3A:
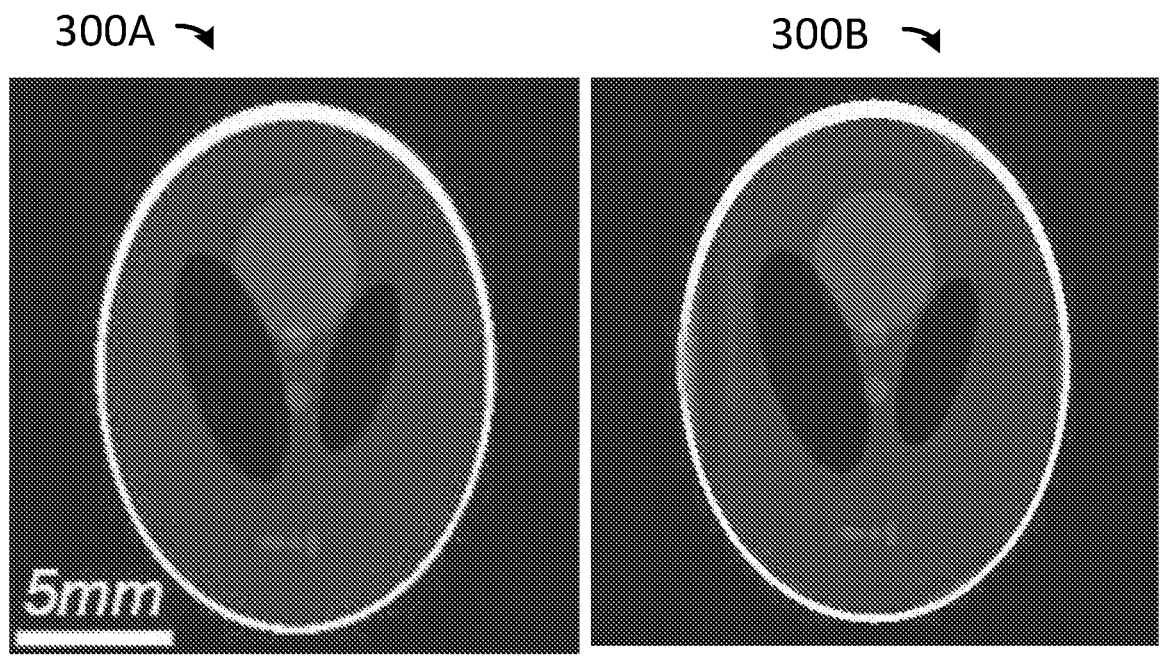
FIG. 3A illustrates a true and reconstructed Shepp-Logan phantom according to an embodiment of the present disclosure.
Figure 3B:
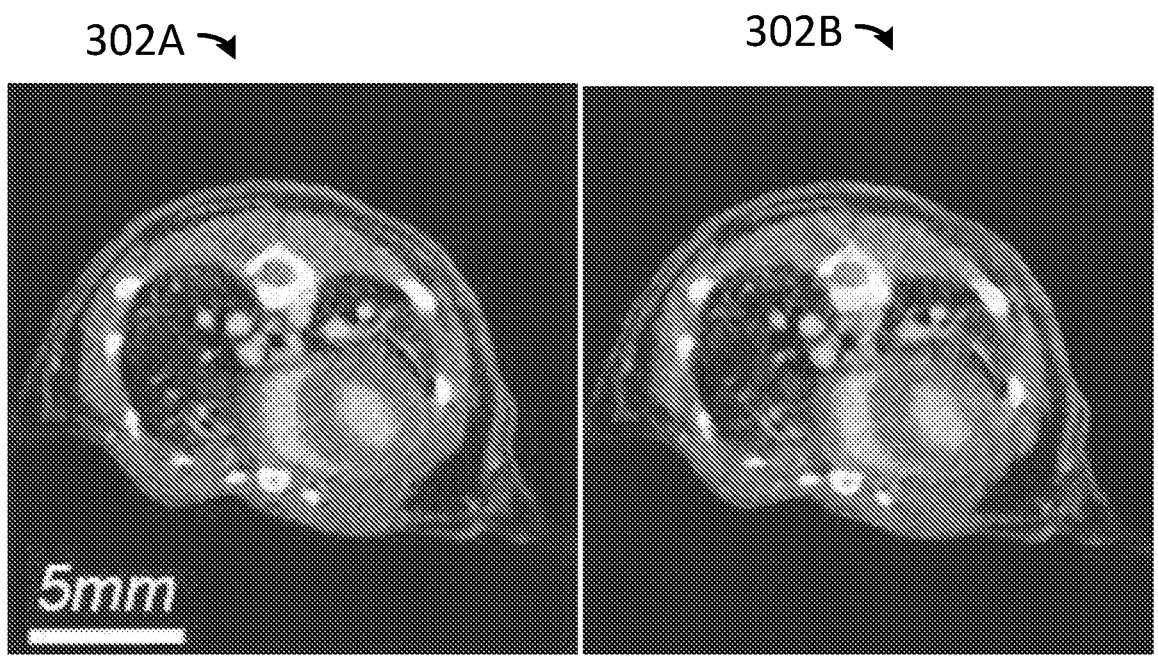
FIG. 3B illustrates a true and reconstructed slice through a mouse chest, according to an embodiment of the present disclosure.

FIG. 3A illustrates a true 300A and reconstructed 300B Shepp-Logan phantom according to an embodiment of the present disclosure. FIG. 3B illustrates a true 302A and reconstructed 302B slice through a mouse chest, according to an embodiment of the present disclosure. The reconstructed images 300B, 302B were determined using a SIGMA system, as described herein. Each imaging chain produced a limited-angle scan of 20 projections around a horizontally placed mouse over a range of (−200, 200). The images were reconstructed based, at least in part, on a compressed sensing (CS) technique.

It is contemplated that changes in mineral shape, size, and orientation affect fracture propensity of bone and that such changes can be measured through x-ray small-angle scattering signals. For example, compared to controls, bones with tumor undergo similar changes in mineral size, shape, and orientation as bone with lower fracture properties. Such changes in bone mineral properties can indeed influence cancer malignant progression. Thus, a SIGMA system according to the present disclosure may be capable of measuring such changes in x-ray tri-contrasts in terms of attenuation, phase shift, and small-angle scattering properties.

Turning again to FIG. 1, each x-ray source array includes a plurality of x-ray source elements. Each x-ray source element corresponds to one x-ray spot. Thus, a size of an x-ray spot and a resolution of the imaging chain is related to a configuration of the x-ray source element.

Figure 4:
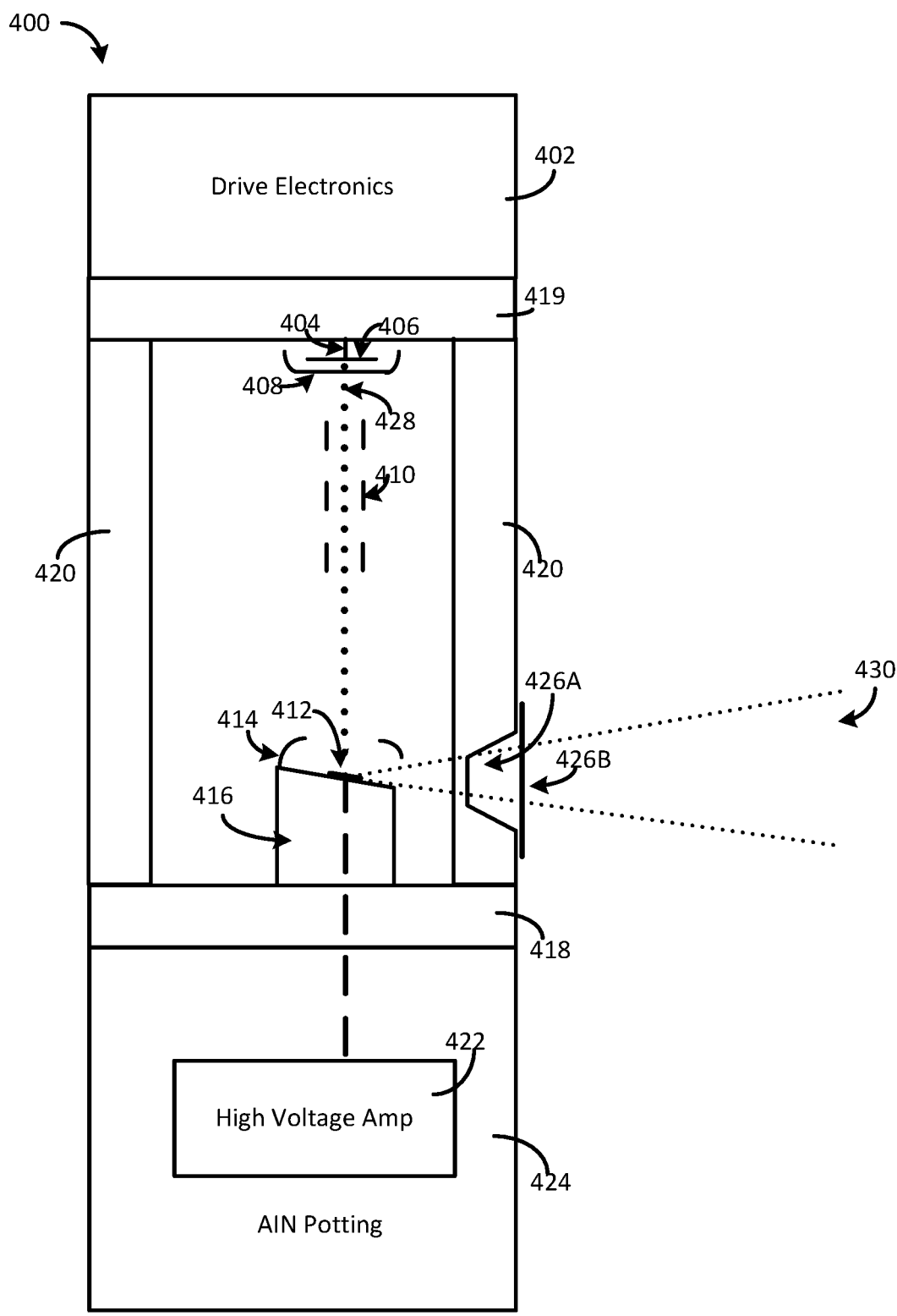
FIG. 4 illustrates an example x-ray source element according to an embodiment of the present disclosure.

FIG. 4 illustrates an example x-ray source element 400 according to an embodiment of the present disclosure. In one embodiment, the x-ray source element 400 may correspond to or be adapted from the DAXS (digitally addressable x-ray source) technology available from Stellarray. X-ray source element 400 includes drive electronics 402, cathodes 404, a gate 406, a focus/shield 408, a focusing column 410, an anode 412, an anode shield 414, a block 416, a base plate 418, a top plate 419, sidewalls 420, a high voltage amplifier 422 and AlN (aluminum nitride) potting 424. The high voltage amplifier 422 may be included in potting 424. X-ray source element 400 may further include a first window option 426A and/or a second window option 426B. X-ray source element 400 may then be configured to generate electronic beams (E-beams) 428 for transmission through window 426A or 426B as x-ray beam 430.

For example, an array of field emission cold cathodes 404 may be positioned above a long, angled (line focus) metal anode 412. Cathodes 404 may be individually addressed via matrixed gate lines to emit electron beams 428 that are focused to the desired locations on the anode 412 (x-ray pixel ("xel") spots). In one nonlimiting example, the field emission cold cathode 404 may use a lateral triple point (LTP) design which can generate current (e.g., >1 mA pulses from a 25 μm line focus emitter cross section). Cathodes 404 may be formed as long ribbons to match the line focus spots on the anode 412. Current extraction may be with lithographically-formed symmetrical gate structures, e.g., gate 406, that can produce e-beams with very small lateral component for easier focusing by the focusing column 410.

Base plate 418, top plate 419 and sidewalls 420 may be configured to form a vacuum enclosure. The top plate 419 and sidewalls 420 may be formed of molded borosilicate glass (BSG) and the base plate 418 may be formed of an anode assembly made of metal or high-thermal conductivity ceramic such as Aluminum Nitride (AlN) to allow direct cooling from outside the panel. A raising block, e.g., block 416, of metal or ceramic is configured to support the top anode 412 surface (1 mm W strip) receiving the e-beams 428 and keeping it electrically isolated from the walls to mitigate internal arcing. The high voltage amplifier 422 potted in AlN material 424 and control electronics 402 may be respectively attached to the bottom and top of the source to avoid the need for bulky cables and connections. The design and metal-glass-ceramic construction of x-ray source array is configured to allow safe, stable operation at up to 100 kV. Each cathode element can be addressed in under 1 μs by its gate to emit its e-beam to one anode spot. In some embodiments, an anode current measurement circuit may be included for control of current and x-ray flux.

In another example, the x-ray source element 400 may include high current density cold cathodes, glass vacuum packaging, compact high voltage power supplies and digital addressing circuits. Permanently-sealed x-ray source elements may be included in top-emitting panels with a 4×30 array of micro-fabricated cold cathodes and side-emitting panels with a 1×30 array of mini-fabricated cold cathodes. The linear array panels may include a molded BSG (Corning 7056), which is thermally matched to a metal (Kovar, TZM) anode assembly that formed another part of the vacuum (10-7 Torr) enclosure. A top metal plate of the anode has a 1 mm W target brazed to receive e-beams from the cold cathode array. A 10 mm thick metal anode base served as a heat sink. Outside forced air or oil cooling is not needed owing to the relatively low power load (~1 kW for <10 msec) on the anode, which may be potted in an electrically insulating epoxy.

The cold cathodes (CNT ropes) may have an emission cross-section of 300×1200 µm for a 300 µm apparent spot. Field emission gating may be provided by matrixed gate leads with parallel 100 µm wires flanking either side of the cathode. These cathodes may obtain a relatively consistent 10 mA up to 5,000,000 pulses before debris starts degrading the vacuum. "Layered triple point" (LTP) cold cathodes may be used in addition or as an alternative to CNTs. Field enhancement in cold cathodes can be provided not only by the aspect ratio of the emitter (tall tips, thin edges) but also by TPs, which are an intersection of the conductor, insulator and vacuum. The TP cathodes may be formed by depositing alternating conductive and insulating thin film layers (50-100 Å) on lithographically-patterned substrates or on thin metal ribbons or other pre-forms for mini-fabricated cathodes that can be assembled into arrays. A first or a second material set may be used. The first, called NLC for nano-layered carbon, is made of numerous, alternating laser-ablated films of graphitic and diamond-like carbon. The second, called MOCA, is made of the same kind of film stack, but of Mo and diamond-like carbon. When the emitting cross-section is revealed, these cathodes have a large number of possible emission sites, since field emission is enhanced at grain (or layer) boundaries. The interfaces between the conducting Mo and insulating diamond layers form TPs when exposed to vacuum, as do the graphitic and diamond films in NLC. The diamond has a low work function, and electrons tunnel from the Mo layer through the edge of the diamond for even better emission.

the pusher directs the electrons up from the substrate and towards the anode. The 50 µm xel cathode may achieve 1.2 mA in the pulsing mode. An LTP cathode using pre-forms is relatively simpler and more robust and may allow separate testing of mini-fabricated cathodes before they are assembled into an array. A Mo ribbon pre-form thinned down to 20×160 µm may correspond to about a 5 µm DAXS xel with focusing and an 8-layer NLC film on either side. This can be trimmed using a focused ion beam tool to reveal the emitter edge. It was tested in the pulsing mode to 2.4 mA at 10-6 Torr vacuum (equivalent to >73 A/cm2). It was then left running in the DC mode for 10 hours (equivalent to over 300,000 10 ms pulses).

In another nonlimiting example, the x-ray source arrays may be modeled on a Hamamatsu L10101 microfocus tube, which is operable to up to 100 kV and 200 mA on spot size ranging from 50 µm down to 5 µm, with maximum power of 20 W. Each x-ray source array may correspond to an array of these microfocus tubes. In other words, each microfocus tube corresponds to an x-ray source element. In one nonlimiting example, the SIGMA system may include three x-ray source arrays with 50 µm focal spot size, 50 µm xel line focus spots and 40 xels in a linear array. In another nonlimiting example, the SIGMA system may include three x-ray source arrays with 5 µm xel line focus spots and 40 xels. The x-ray source arrays in this example may include AlN components, relatively thinner windows an integrated high voltage amplifier and associated control electronics.

A limiting factor for current (and thus x-ray flux) is the instantaneous power load on the anode spot, which could sublimate or pit a W target. Table 2 includes x-ray source element operating parameters and associated factors. In particular, Table 2 provides cathode current densities and spot power loading calculations for different xel parameters.

TABLE 2

| | | | | | | | | | | |
|---|---|---|---|---|---|---|---|---|---|---|
| Voltage | kVp | 40 | 40 | 40 | 80 | 80 | 80 | 100 | 100 | 100 |
| Current | µA | 1250 | 310 | 12.5 | 620 | 155 | 6.2 | 500 | 125 | 5 |
| Power | W | 50 | 12.4 | 0.5 | 49.6 | 12.4 | 0.496 | 50 | 12.5 | 0.5 |
| Apparent focal spot width | µm | 50 | 25 | 5 | 50 | 25 | 5 | 50 | 25 | 5 |
| Line focus factor | # | 5 | 5 | 5 | 5 | 5 | 5 | 5 | 5 | 5 |
| Spot area, line focus | µm$^2$ | 12500 | 3125 | 125 | 12500 | 3125 | 125 | 12500 | 3125 | 125 |
| Spot current density (native) | A/cm$^2$ | 10.0 | 9.9 | 10.0 | 5.0 | 5.0 | 5.0 | 4.0 | 4.0 | 4.0 |
| Current focus factor | # | 2 | 4 | 20 | 5 | 5 | 5 | 5 | 5 | 5 |
| Current density at anode | A/cm$^2$ | 5.0 | 2.5 | 0.5 | 1.0 | 1.0 | 1.0 | 0.8 | 0.8 | 0.8 |
| Anode spot power density | kW/mm$^2$ | 4.0 | 4.0 | 4.0 | 4.0 | 4.0 | 4.0 | 4.0 | 4.0 | 4.0 |
| Grooved anode density | kW/mm$^2$ | 2.0 | 2.0 | 2.0 | 2.0 | 2.0 | 2.0 | 2.0 | 2.0 | 2.0 |

A small format (<100 µm) LTP cathode array may be one of two designs, both of which may exceed the current capability of selected Hamamatsu source(s). An example micro-fabricated design may include a disk pusher cathode (DPC), in which separately ballasted and gated lateral tip emitters are formed on Si substrates face inwards and emit towards a central pusher electrode, the diameter of which defines the cathode xel size. A negative voltage applied to An initial power load limit of 4 kW/mm$^2$ may allow delivery of a sufficient current at 40 kV. Anode improvements may include, but are not limited to, etching grooves in the xel spots, and making ridged targets by etching the W and depositing diamond or Cu to either side for improved heat transfer, which could relax the load limit and allow further increases in acquisition speeds. Thus, x-ray source arrays may correspond to linear arrays of 5 µm anode spots with 3× higher current than selected microfocus tubes, <1% variation xel to xel in x-ray flux, and integrated panels (including power supplies and controls) under 4,000 cc in volume.

Current from cold cathodes with relatively larger cross sections may be focused down with electrostatic columns to relatively small xel spot areas on the anode. As shown in Table 2, relatively little focusing of the e-beams may be utilized for 50 μm spots but stronger focusing may be utilized for 5 μm. Focusing designs may be modeled in 2D using the Simion package, and/or relatively more fully explored in 3D models created with COMSOL, which may be verified with prototype emitter section (cathodes, gates, first focus plate, and focus column) testing in a demountable vacuum chamber. In one nonlimiting example, the cold cathodes may be LTP-style with 50 μm and 5 μm anode spots. The cathodes may be made using metal pre-forms (20 μm Mo ribbons, etched for further sharpness) with MOCA or NLC films deposited on the sides using a multi-source tool, and then the emitting edge or point revealed by FIB, reactive ion etch, polishing or masking during the film deposition process. The number of films, thickness, and treatments such as plasma etching are variables for current density performance. Wet etching may be done of Mo in some devices so as to make the diamond film edges protrude slightly to enhance field strength and electron tunneling through the diamond. The mini-fabricated cathodes may be assembled into gated busses and tested for I-V characteristics in DC and pulsed modes. Pulsing may use 5 or 10 sec pulse widths. The cathodes may be incorporated into an emitter assembly, which is basically a stack of plates or bars separated by ceramic shim. The cathode plate may be made of ceramic or Si with the apertures (e.g., 50×250 μm or 25×125 μm) machined or etched through to hold the cathodes. The apertures may be slightly angled to make the e-beams and thus the focus on the anode line up with the collimator outside the window to make most efficient use of the flux. A metal address line may be deposited over the cathodes along the length of the plate. The gate plate may have the same construction but with parallel gate lines photolithographically formed or fine wire bonded perpendicular to the cathode line and attached to address leads running through the top plate of the source to the drive electronics. The metal focus plate may be positioned beneath this assembly with aperture size determined by electrostatic modeling and focus tests. Additional focus/lens structures may be suspended and electrically isolated from this plate, with voltage address lines running through the top glass of the source. The focusing plates may be processed together, or with one plate being the template for the next so that the apertures are all self-aligned. The currents indicated in Table 2 are within the range of existing ribbon-style LTP cathodes. If more current is needed, ribbons can be ganged together side-by-side, and additional gate wires run between them. The full emitter structures may be tested in the demountable chamber for emission performance in pulsed, DC and lifetime modes, and with anode and walls in the demountable for electrostatic stability.

Fabrication of x-ray source arrays may include modeling. For example, COMSOL may be used to model panel electrostatics to design out internal arcing factors such as unwanted TPs. Anode thermal characteristics may be modeled with the Elmer thermal modeling package. Grooved anodes and other surface modifications may be modeled to design in higher anode power density. Most of the power may spread quickly in the 1 mm W target surface, and the brazed interface may be important for bulk thermal transfer.

Modeling results may be verified with tests using thermal stacks of different materials connected with the designed interfaces (e.g. brazing), with temperature sensors positioned at each level of the stack. Anodes may be tested in a demountable vacuum chamber with increasing spot power loads and examined for ablation or pitting.

As shown in FIG. 4, the flux exit window 426A, 426B at the side of the source 400 can be made either by machining a long recess into the side glass or by forming an aperture straight through and then sealing a thin plate window outside with the desired attenuation, e.g. 200 μm thick BeO, SiN, AlN or diamond. Sealing methods may include, but are not limited to frit, adhesive, compressed metal seal. For example, recessed glass (<1 mm thick) may be used, with the thin plate windows used in the subsequently deliverable sets.

In one nonlimiting example, initially the panels may use TZM metal anode base plates, with Aluminum Nitride base plates and raising blocks incorporated once frit-sealing methods are tested. AlN has outstanding thermal conductivity (92-200 W/mK, depending on the grade, for a good match with W) and very high dielectric strength (65 kV/mm-ac for Shapal, a machinable form) so that 10 mm of wall thickness may provide good electrical insulation for sources to 100 kVp. AlN's coefficient of thermal expansion of 5.3 ppm is closely matched with the W, BSG and other source materials, for mechanical integrity during sealing and operation.

To make the x-ray source arrays as compact as possible, the high voltage amplifier (HVA) and the emitter section electronics may be integrated into the source module. The HVA may be encased in an AlN compound (Aremco 675-N, Valley Cottage, N.Y.), with connections to the anode strips through the AlN base plate and raising block. The length of the cathode array 404 may be 200 mm. When walls and electrical spacing are added, dimensions may be approximately 250 mm long×200 mm high×70-100 mm wide per source array.

A glass pump-out tube may be used for evacuation and sealing of a first panel set. A "tipless" sealing method using a frit or Au/Ti eutectic plug and removable metal pump-out tube may also be used for improved compactness and ruggedness. Sources may be tested in a demountable chamber for electrical performance and arc incidence. They may be sealed and prepared for vacuum pump out. Source vacuum levels may be measured before final pump-out tube sealing using, for example, an SRI residual gas analyzer. Angled collimator arrays made of a W alloy substitute for lead may be fabricated and mounted outside the window for global and interior scans.

The HV amplifiers, e.g., high voltage amplifier 422, may have a relatively low profile format using thin capacitors available from, for example, Novacap (Santa Clarita, Calif.). The HV amplifiers may be encased in AlN mold or epoxy and AlN powder. Drive electronics 402 may include IGBTs configured to allow gate switching up to 2,000V. Gate switching of approximately 500V may be implemented with close (approximately 50 μm) spacing between the cathode 404 and gate plates 406. The drive boards may then be potted or encased at the top of the panel. Demountable and sealed panel testing may be performed as described above. Xels may be driven to the desired current (0.05-1 mA), depending on the anode spot size, for up to 100,000 pulses using a pulse test circuit previously developed. Panels may be tested for at least 1,000 hours lifetime.

A negligible xel-to-xel current and flux variation may be accomplished by a variation in pulse width controlled by feedback from the anode current sensor. X-ray flux generation from individually addressed xel spots in sealed sources may be measured in a radiation test room using a Radcal detector for flux intensity and an Amtek 123 spectrophotometer for the spectrum from selected sources. An IEC standard pinhole phantom with different flux spot apertures may be used to measure the effective focal spots sizes of the xels.

Thus, each x-ray source array may include a plurality of x-ray source elements. Each x-ray source element may then correspond to x-ray source element 400.

Figure 5A:
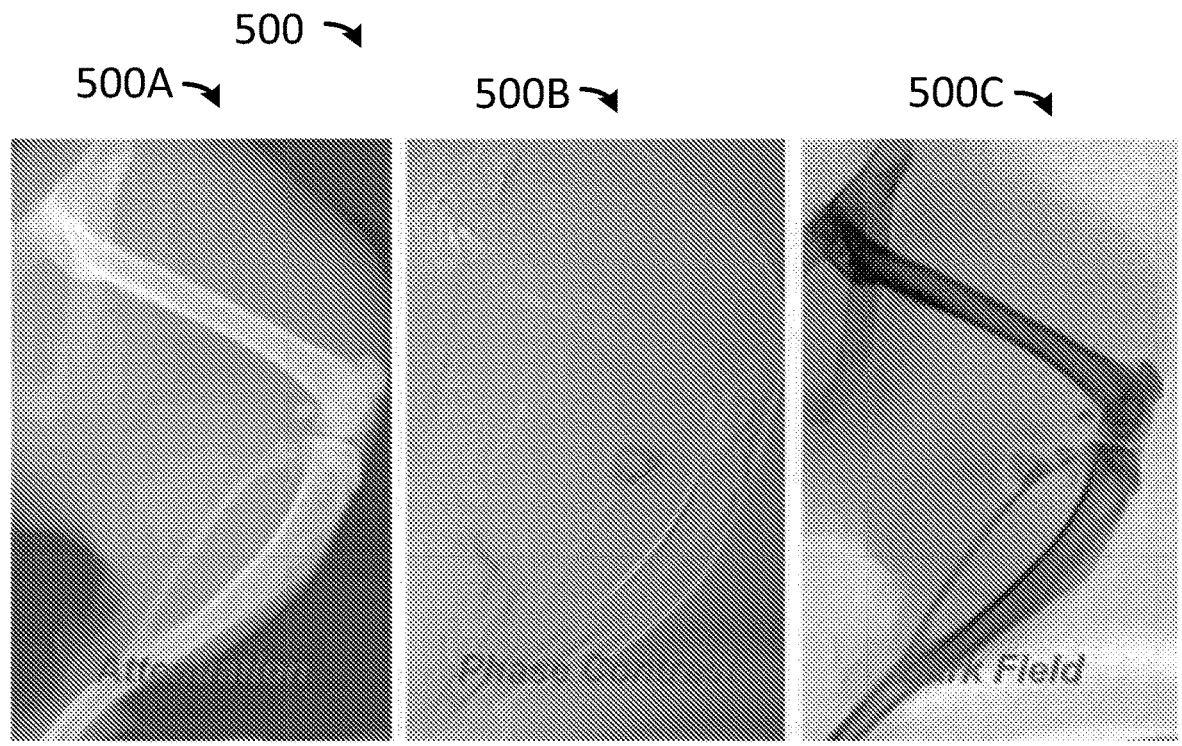
FIGS. 5A and 5B illustrate two example micro-CT tri-contrast image reconstructions according to an embodiment of the present disclosure.
Figure 5B:
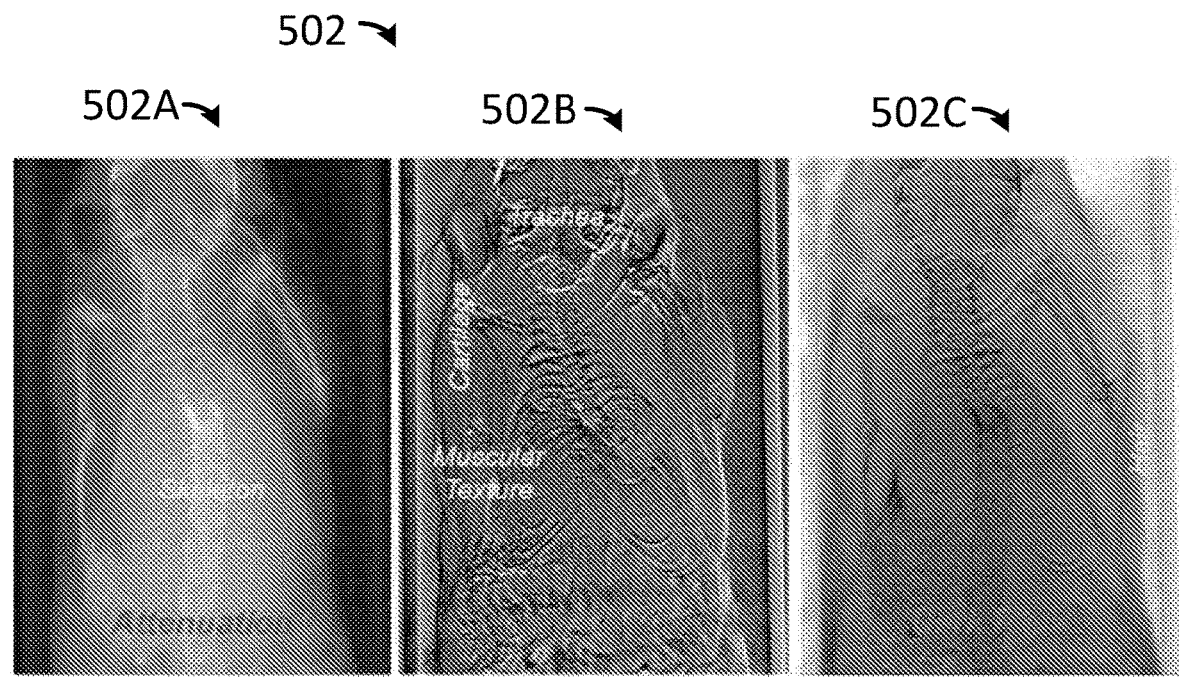

FIGS. 5A and 5B illustrate two example 500, 502 micro-CT tri-contrast image reconstructions according to an embodiment of the present disclosure. A first example 500 is a micro-CT tri-contrast image of a mouse bone sample. The tri-contrast images of the first example 500 include attenuation 500A, phase contrast 500B and dark field (small angle scattering) contrast 500C of the mouse bone sample. A second example 502 is a micro-CT tri-contrast image of a whole mouse. The tri-contrast images of the second example 502 include attenuation 502A, phase contrast 502B and dark field (small angle scattering) contrast 502C of the mouse.

The tri-contrast images 500, 502 were acquired using an example Talbot interferometer that included a microfocus x-ray source (Hamamatsu L10101), an x-ray CMOS flat panel detector Rayence 1215MGF, and Microworks 1D gratings for 28 KeV x-rays. The protocol parameters include 40 kVp and 200 µA, 1 fps for the x-ray detector, 4.24 µm G1, 2.4 µm G2, duty cycle 55%, 1$^{st}$ order Talbot effect, a 435 mm G1-to-source distance, a 15 mm G1-to-mouse distance, 57.4 mm G1-to-G2 distance, 5 phase steps with G2 over approximately 50 seconds, and approximately 10% visibility.

Figure 5C:
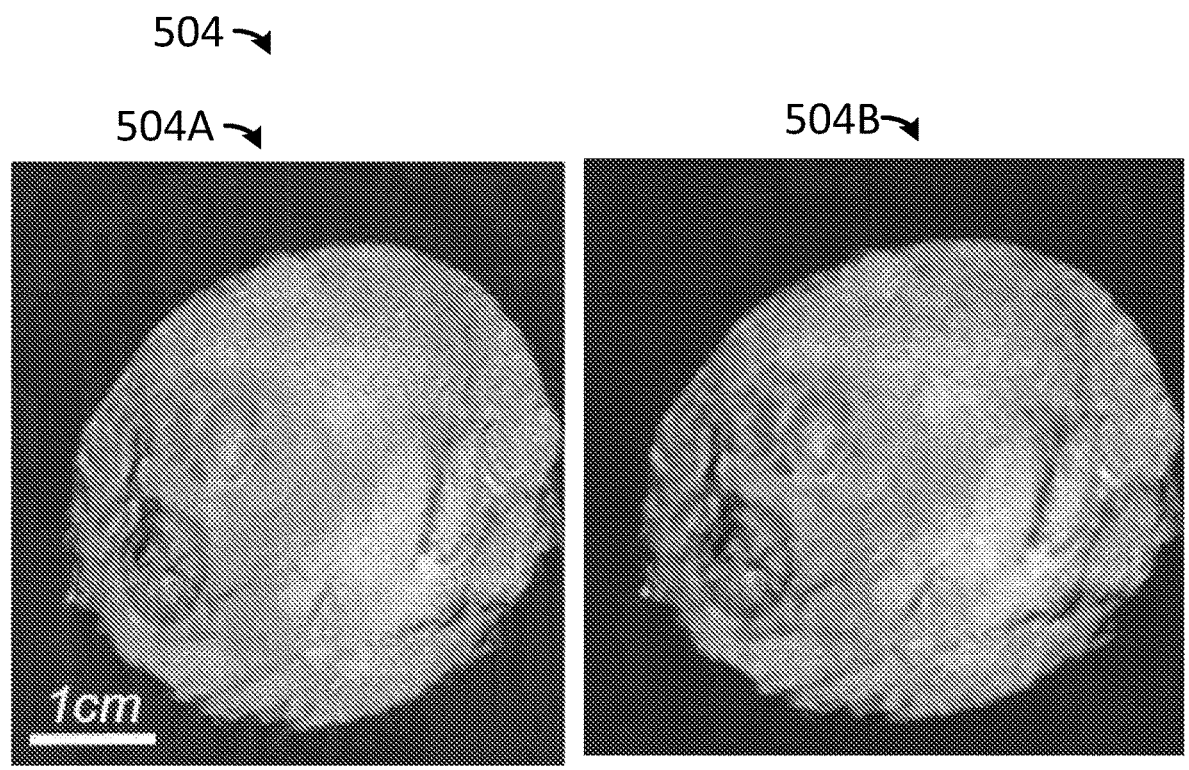
FIGS. 5C and 5D illustrate two example phase contrast image reconstructions using a CS method according to an embodiment of the present disclosure.
Figure 5D:
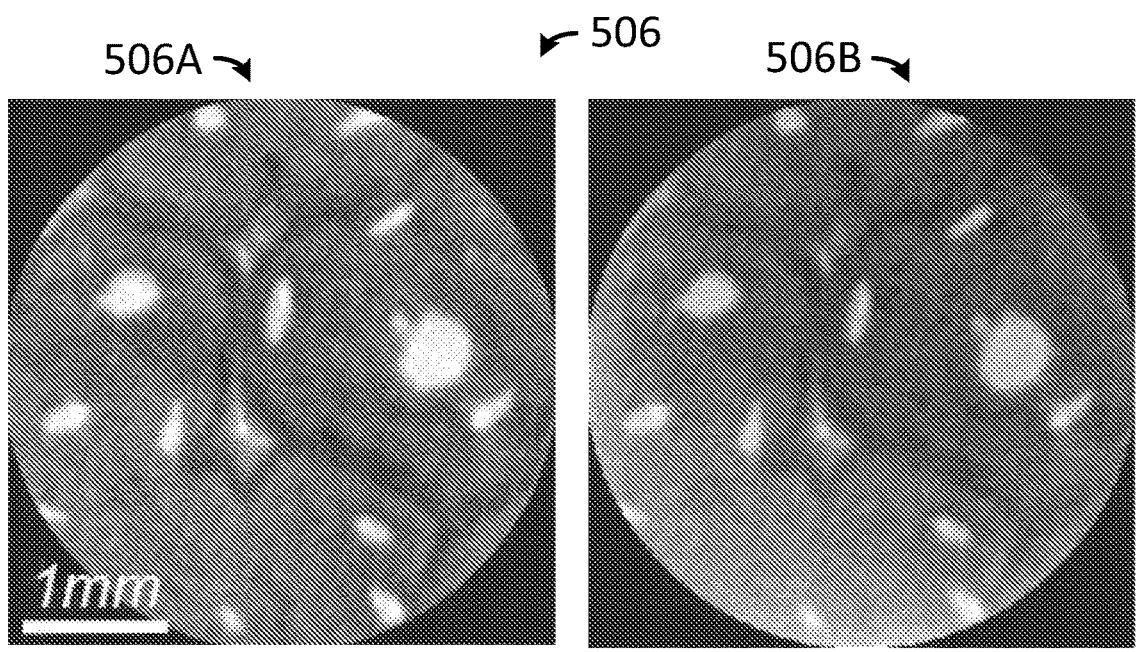

FIGS. 5C and 5D illustrate two example 504, 506 phase contrast image reconstructions using a CS (compressed sensing) method according to an embodiment of the present disclosure. A first example 504 is a phase contrast global reconstruction of a rabbit liver. The phase contrast image reconstructions include an image 504A reconstructed from 251 views with filtered backprojection (FBP) and an image 504B reconstructed from 60 projections using the CS method. A second example 506 is a phase contrast interior reconstruction of a mouse bone sample. The phase contrast image reconstructions include an ROI 506A in the global image reconstructed with FBP, and an interior reconstruction 506B from 60 projections using the CS method.

For the example 504, 506 phase contrast image reconstructions, a rabbit liver and mouse bone samples were studied using an x-ray Talbot interferometer. Moiré patterns were recorded on a CCD camera with a phosphor screen and an optical lens. For each view, the G2 grating was translated in 5 steps. Then, few-view global and interior images were reconstructed using the compressed sensing (CS) inspired techniques as illustrated in FIGS. 5C and 5D.

Turning again to FIG. 1, few view circuitry 120 may be configured to implement few view image reconstruction. The limited-angle imaging geometry of the SIGMA system is configured to utilize three symmetrically distributed limited-angular ranges to sample the Radon space. Unlike traditional CT image reconstruction that utilizes hundreds or a thousand projections, the few-view tomography technique uses on the order of 100 projections and is configured to work in a compressed sensing (CS) framework. A CS technique known as dictionary learning (DL) may be utilized for few view reconstruction. In contrast to the total variation (TV) approach, a dictionary learned from samples may be relatively more effective in terms of a sparse representation. A DL-based reconstruction algorithm for low-dose CT may perform relatively better than the TV-based reconstruction. A relatively popular DL method is based on K-SVD and is configured to take images as vectors. In a multi-dimensional space, vectorization may overlook structural correlation. Thus, a SIGMA system according to the present disclosure may be configured to implement a tensor-based DL approach.

Figure 5E:
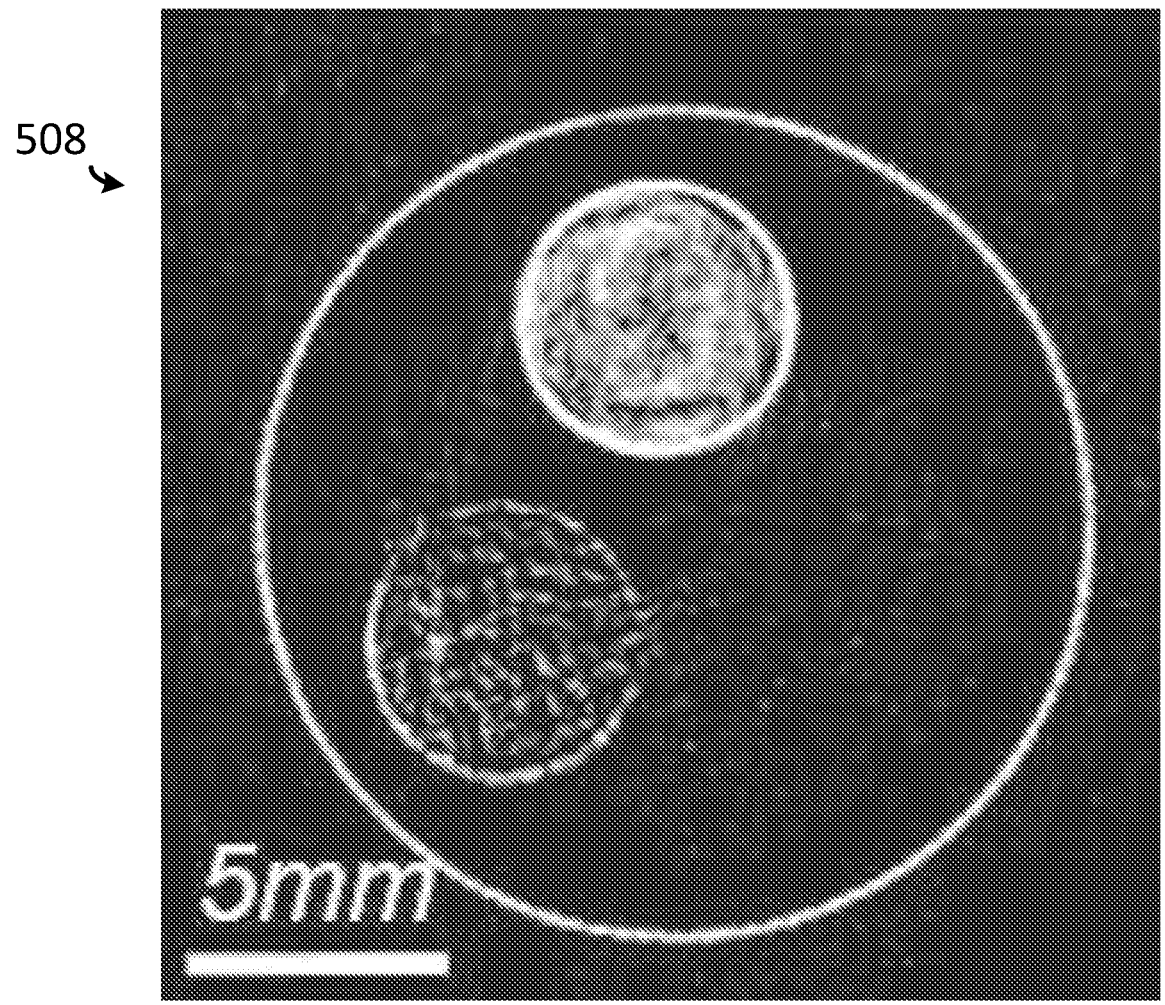
FIG. 5E illustrates an example dark field phantom reconstructed based on a small angle scattering model according to an embodiment of the present disclosure.

FIG. 5E illustrates an example 508 dark field phantom reconstructed based on a small angle scattering model according to an embodiment of the present disclosure. Dark-field images are formed from x-ray small-angle scattering signals. A relationship between x-ray small-angle scattering coefficients of an object and dark-field intensity images is configured to describe the small angle scattering signal propagation through an object, based on the principle of energy conservation. This model can be used to reconstruct volumetric x-ray small-angle scattering images of an object using classical tomographic techniques. A relationship between the small-angle scattering intensity and the visibility function measured using x-ray grating-based phase-stepping techniques has also been established. Numerical simulations and phantom experiments have demonstrated the accuracy and practicability of the model. It should be noted that changes in bone mineralization with bone metastasis affect the x-ray small-angle scattering signals significantly.

In an x-ray grating-based interferometer, the phase grating is a periodic phase mask, which transforms coherent x-ray waves into a periodic pattern with intensity modulation on the detector plane. The interference fringes (Talbot fringes) are produced as self-images of the phase grating, which has a period smaller than the pixel size of the current commercial detector array. By performing the phase stepping, the analyzer grating (G2) is translated with a step size of a fractional Talbot fringe period, recording x-ray intensity images to measure sample-induced fringe deformations. Then, the transmission, differential phase shift, and dark field signals can be extracted from these images using a Fourier analysis method.

A differential phase shift data $\partial_s \Phi(s, \theta)$ may be directly extracted from data measured with the SIGMA system.

Because the phase shift $\Phi(s, \theta)$ is a projection of a refractive index function $\delta(r)$, the following differentiated backprojection (DBP) formula describes the relationship between the refractive index and the differential phase shift:

$$H\delta(r) = -\frac{\lambda}{4\pi^2} \int_{\theta}^{\theta+\pi} \frac{\partial}{\partial s}(s, \varphi)|_{s=r\alpha} \, d\varphi \quad (1)$$

where $H\delta(r)$ is a Hilbert transform of the refractive index function $\delta(r)$. Based on Eq. (1), the image reconstruction can be achieved with the inverse Hilbert transform, which can be implemented using an iterative technique to suppress image noise at an additional computational cost. For dark field imaging, a small-angle scattering model based the principle of energy conservation may quantitatively describe a relationship between the small-angle scattering coefficients $\mu_s(r)$ and the measured dark field signal:

$$\ln\left[1 + \frac{T_s(r+R\theta)}{T_a(r+R\theta)}\right] = \int_0^R \mu_s(r+s\theta)ds \quad (2)$$

where $T_a(r+R\theta)$ and $T_s(r+R\theta)$ are transmission signals in attenuation and dark-field data respectively. Eqs. (1), (2) and the Beer law may then be used for x-ray tri-contrast image reconstruction.

Based on Eqs. (1) and (2), images may be reconstructed using a dictionary learning (DL) approach. DL may be used to facilitate few-view CT reconstruction. The DL-based method may be extended from a vectorized dictionary to a tensor dictionary for image reconstruction in tri-contrasts. The tensor dictionary is configured to capture correlated multi-channel features effectively. A training set of tensor patches can be extracted from reference images reconstructed from high-quality datasets collected in high dose over long time. Given a training set of tensor patches $x_s \in R^{M \times N \times L}$ (s=1, 2, ..., S) from high-quality images, a tensor dictionary can be built by requesting each patch in the training set to be sparsely represented by atoms of the dictionary. This is a minimization problem:

$$\min_{D, \alpha_s} \sum_{s=1}^{S} (\|x_s - D * \alpha_s\|_F^2 + v_s \|\alpha_s\|_0) \quad (3)$$

where the dictionary $D \in R^{M \times N \times L}$ consists of tensor atoms, $\alpha_s$ is a sparse representation, and '*' denotes the product of tensors. Eq. (3) may be minimized via K-CPD. Then, an image may be reconstructed as follows:

$$\min_{x, \alpha} \|A * x - b\| + \beta \sum_{s} (\|\varepsilon_s(x) - D * \alpha_s\|_F^2 + v_s \|\alpha_s\|_p) \quad (4)$$

where A is a system matrix discretized from Eq. (1) and (2), $\varepsilon_s$ is an operator to extract patches from a tensor image $x \in R^{M \times N \times L}$, and $\|\cdot\|_p$ is a $l_p$-norm (0<p≤1). Eq. (4) can be efficiently solved using the split-Bregman iteration through separated $l_2$ and $l_1$ minimizations. The conjugate gradient method may then be used to solve the $l_2$ minimization. The fast iterative shrinkage-thresholding technique may be utilized to manage the $l_1$ minimization. Different from either the TV-based reconstruction or the nonlocal-mean-based reconstruction, the DL-based approach relies on a knowledge database (the dictionary) to perform task-specific reconstruction.

Thus, CT image reconstruction circuitry 120 may be configured to implement micro-CT image reconstruction based, at least in part, on CT data including tri-contrasts (attenuation, phase contrast and small angle scattering), and few view image reconstruction. Image reconstruction may include iterative techniques. In one nonlimiting example, image reconstruction may be performed on a graphical processing unit (GPU). In another nonlimiting example, to accelerate reconstruction, image reconstruction may be performed by a plurality of GPUs. DL-based reconstruction is generally parallel thus, parallel processing aspects of GPU(s) may be exploited in order to achieve a target less than five minutes volumetric image reconstruction from a circular mouse scan.

Figure 6:
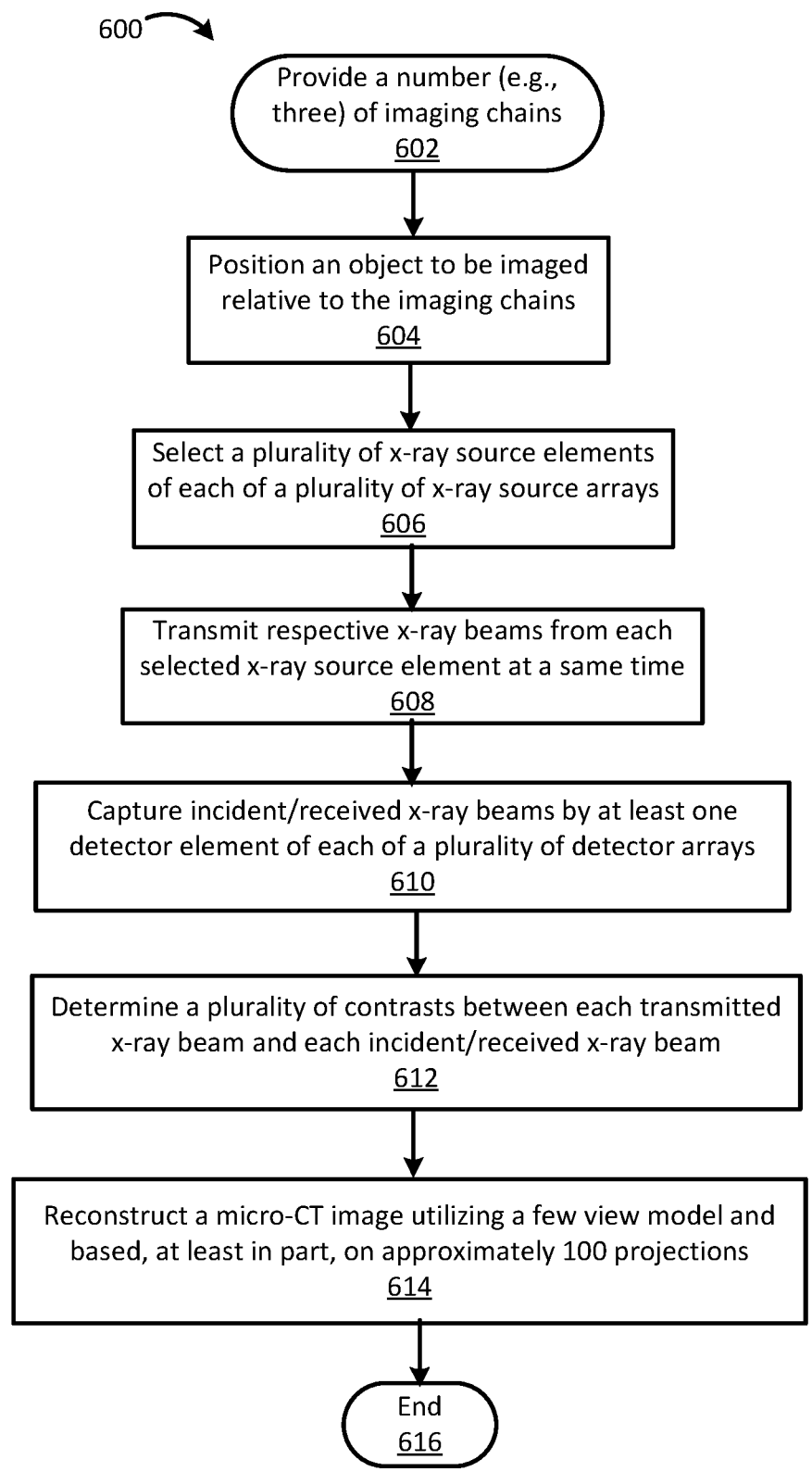
FIG. 6 is a flowchart of example SIGMA system operations consistent with several embodiments of the present disclosure.

FIG. 6 is a flowchart 600 of example SIGMA system operations consistent with several embodiments of the present disclosure. In particular, flowchart 600 illustrates determining an in-vivo grating-enabled micro-CT image utilizing a SIGMA system, consistent with the present disclosure. The operations of flowchart 600 may be performed by, for example, imaging chains 104-1, 104-2, 104-3 and/or CT scanner control circuitry 102 of FIG. 1.

Operations of flowchart 600 may begin with providing a number (e.g., three) of imaging chains at operation 602. Each imaging chain includes an x-ray source array, a phase grating, an analyzer grating and a detector array. Operation 604 may include positioning an object to be imaged relative to the imaging chains. For example, the object to be imaged may be positioned at a center point corresponding to an intersection of centerlines associated with the imaging chains. A plurality of x-ray source elements of each of a plurality of x-ray source arrays may be selected at operation 606. Operation 608 may include transmitting respective x-ray beams from each selected x-ray source element at a same time. Incident/received x-ray beams may be captured by at least one detector element of each of a plurality of detector arrays at operation 610. A plurality of contrasts between each transmitted x-ray beam and each incident/received x-ray beam may be determined at operation 612. For example, the plurality of contrasts may include linear attenuation, phase shift and small angle scattering. A micro-CT image may be reconstructed utilizing a few view model and based, at least in part, on approximately 100 projections at operation 614. Program flow may then end at operation 616.

Thus, an in-vivo grating-enabled micro-CT image may be determined utilizing a SIGMA system.

Generally, this disclosure relates to a stationary in-vivo grating-enabled micro-CT (computed tomography) architecture (SIGMA) system. An apparatus, method and/or system are configured to replace mechanical x-ray source rotation (i.e., gantry rotation) with electronic multiplexing facilitating x-ray interferometry by providing micron-level alignment. The apparatus, method and/or system includes three stationary imaging chains that may be operated in parallel. Each imaging chain includes x-ray gratings (phase grating, analyzer grating), an x-ray source array and a detector arrays. Each x-ray source array includes a plurality of x-ray source elements that may be selected electronically and operated individually. Each x-ray source element may be configured to provide an x-ray spot of a defined size corresponding to an x-ray beam configured to encounter an object to be imaged. The apparatus, method and/or system may be further configured to include few-view image reconstruction, as will be described in more detail below.

In an embodiment, the SIGMA system includes three imaging chains that may be used in parallel, thus tripling the imaging speed. Each imaging chain may thus include an x-ray source array, a phase grating, an analyzer grating and a detector array. The source arrays may be symmetrically arranged along with the corresponding detector array, and phase and analyzing gratings between the source and detector. Each imaging chain may be configured to perform a limited-angle scan via electronic manipulation of x-ray focal spots.

The SIGMA system may be configured with two non-overlapped regions on each detector array that are used for data collection in parallel. Two x-ray spots in each source array are turned on to cast two nonoverlapped projections on the corresponding detector array. The data acquisition efficiency may then be doubled. The few view reconstruction technique is configured to reduce the number of projections by several folds. Thus, the SIGMA system may scan an object an order of magnitude faster than the existing systems without compromising image quality.

Tri-contrast images may be reconstructed from data collected over three limited-angular ranges in a compressed sensing framework providing 30 µm resolution and 30-minute scan time, and characterized in phantom experiments at an x-ray dose level comparable to that of a typical micro-CT scan. Thus, the SIGMA system is configured to provide stable imaging performance at a resolution on the order of 30 µm (micrometers) in x-ray tri-contrasts (i.e., attenuation, phase shift, small angle scattering). The SIGMA system is further configured to provide a scan time of on the order of 30 minutes.

It is contemplated that x-ray tri-contrasts images from the SIGMA system will allow quantification of tumor growth and metastasis in vivo, and analysis of bone architecture, mineral composition, and collagen content for better diagnosis and management of bone metastasis. For example, the SIGMA system may improve diagnosis of osteoarthritis (OA) that involves mineralization of cartilage, type 2 diabetes (T2D) and osteoporosis. Thus, a SIGMA system, according to the present disclosure, may then be utilized for detecting and quantifying bone metastasis, senile and postmenopausal osteoporosis, T2D, OA, etc. For example, the 30 µm resolution may provide the ability to resolve structural units of bone or osteons in the order of 200 µm in size, which are altered with tissue remodeling.

It is further contemplated that an apparatus, system and/or method may be utilized to characterize ex vivo human bone tumor samples and live mouse models with bone metastasis. For example, cadaveric human lumbar and thoracic spine, containing osteolytic, osteoblastic, and mixed metastatic bone lesions and controls may be analyzed using the SIGMA system. Bone matrix modification, degree of mineralization, and spatial arrangement of mineral platelets may be determined and compared between diseased and control groups. Mouse models with predominant types of metastasis, expressed in ex vivo human samples, may be used to monitor changes in tumor growth and metastasis. Relevant parameters may be extracted to evaluate metastatic bone. A subset of bones may then be processed for histology and fracture properties.

As used in any embodiment herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

"Circuitry", as used in any embodiment herein, may include, for example, singly or in any combination, hard-wired circuitry, programmable circuitry such as computer processors including one or more individual instruction processing cores, state machine circuitry, and/or firmware that stores instructions executed by programmable circuitry. The logic may, collectively or individually, be embodied as circuitry that forms part of a larger system, for example, an integrated circuit (IC), an application-specific integrated circuit (ASIC), a field-programmable gate array (FPGA), a programmable logic device (PLD), a complex programmable logic device (CPLD), a system on-chip (SoC), etc.

Memory 112 may include one or more of the following types of memory: semiconductor firmware memory, programmable memory, non-volatile memory, read only memory, electrically programmable memory, random access memory, flash memory, magnetic disk memory, and/or optical disk memory. Either additionally or alternatively memory 112 may include other and/or later-developed types of computer-readable memory.

Embodiments of the operations described herein may be implemented in a computer-readable storage device having stored thereon instructions that when executed by one or more processors perform the methods. The processor may include, for example, a processing unit and/or programmable circuitry. The storage device may include a machine readable storage device including any type of tangible, non-transitory storage device, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of storage devices suitable for storing electronic instructions.

What is claimed is:

1. An apparatus for stationary in-vivo grating-enabled micro-CT (computed tomographic) imaging, the apparatus comprising:
a number of imaging chains, each imaging chain comprising an x-ray source array, a phase grating, an analyzer grating and a detector array,
wherein each imaging chain is stationary and each x-ray source array comprises a plurality of x-ray source elements,
wherein each imaging chain has a centerline, the centerlines of the number of imaging chains intersect at a center point and a first angle between the centerlines of a first adjacent pair of imaging chains equals a second angle between the centerlines of a second adjacent pair of imaging chains,
wherein selected x-ray source elements, among the plurality of x-ray source elements, are configured to emit x-ray beams in a multiplexing fashion, and
wherein the apparatus is configured to determine contrasts between each of the emitted x-ray beams and each x-ray beam received at the detector array, and reconstruct a micro-CT image, using a few view model, based on the contrasts.

2. The apparatus of claim 1, wherein each x-ray source array is configured to emit a respective x-ray beam at a same time.

3. The apparatus of claim 1, wherein the number of imaging chains is three, each imaging chain is configured to provide tri-contrasts comprising attenuation, phase shift and small angle scattering and each x-ray source array and each detector array are planar or curved.

4. The apparatus of claim 1, wherein each of the plurality of x-ray source elements is individually digitally addressable.

5. The apparatus according to any one of claims 1 to 4, wherein each x-ray source element has a spot size in the range of 5 µm (micrometers) to 20 µm.

6. The apparatus according to any one of claims 1 to 4, wherein the imaging chains have a resolution on the order of 30 µm (micrometers).

7. The apparatus of claim 1, wherein the imaging chains do not include a micro-focus x-ray tube.

8. The apparatus of claim 1, wherein two x-ray source elements in each source array are turned on at a same time to cast two nonoverlapped projections on a corresponding detector array, among the detector arrays.

9. A stationary in-vivo grating-enabled micro-CT (computed tomography) architecture (SIGMA) system, the SIGMA system comprising:

CT scanner control circuitry; and a number of imaging chains, each imaging chain comprising an x-ray source array, a phase grating, an analyzer grating and a detector array, wherein each imaging chain is stationary and each x-ray source array comprises a plurality of x-ray source elements, wherein each imaging chain has a centerline, the centerlines of the number of imaging chains intersect at a center point and a first angle between the centerlines of a first adjacent pair of imaging chains equals a second angle between the centerlines of a second adjacent pair of imaging chains, wherein selected x-ray source elements, among the plurality of x-ray source elements, are configured to emit x-ray beams in a multiplexing fashion, and wherein the CT scanner control circuitry is configured to determine contrasts between each of the emitted x-ray beams and each x-ray beam received at the detector array, and reconstruct a micro-CT image, using a few view model, based on the contrasts.

10. The SIGMA system of claim 9, wherein each x-ray source array is configured to emit a respective x-ray beam at a same time.

11. The SIGMA system of claim 9, wherein the number of imaging chains is three, each imaging chain is configured to provide tri-contrasts comprising attenuation, phase shift and small angle scattering and each x-ray source array and each detector array are planar or curved.

12. The SIGMA system of claim 9, wherein each of the plurality of x-ray source elements is individually digitally addressable.

13. The SIGMA system according to any one of claims 9 to 12, wherein each x-ray source element has a spot size in the range of 5 μm (micrometers) to 20 μm.

14. The SIGMA system according to any one of claims 9 to 12, wherein the imaging chains have a resolution on the order of 30 μm (micrometers).

15. The SIGMA system according to any one of claims 9 to 12, wherein the CT scanner control circuitry is configured to reconstruct a micro-CT image utilizing on the order of 100 projections.

16. A method for in-vivo grating-enabled micro-CT (computed tomography) imaging, the method comprising:

providing a number of imaging chains, each imaging chain comprising an x-ray source array, a phase grating, an analyzer grating and a detector array, wherein each imaging chain is stationary and each x-ray source array comprises a plurality of x-ray source elements, wherein each imaging chain has a centerline, the centerlines of the number of imaging chains intersect at a center point and a first angle between the centerlines of a first adjacent pair of imaging chains equals a second angle between the centerlines of a second adjacent pair of imaging chains;

emitting, by selected x-ray source elements, among the plurality of x-ray source elements, x-ray beams in a multiplexing fashion; and determining contrasts between each of the emitted x-ray beams and each x-ray beam received at the detector array, and reconstructing a micro-CT image, using a few view model, based on the contrasts.

17. The method of claim 16, further comprising emitting, by each x-ray source array, a respective x-ray beam at a same time.

18. The method of claim 16, further comprising providing, by each imaging chain, tri-contrasts comprising attenuation, phase shift and small angle scattering and wherein the number of imaging chains is three and each x-ray source array and each detector array are planar or curved.

19. The method of claim 16, wherein each of the plurality of x-ray source elements is individually digitally addressable.

20. The method according to any one of claims 16 to 19, wherein each x-ray source element has a spot size in the range of 5 μm (micrometers) to 20 μm.

21. The method according to any one of claims 16 to 19, wherein the imaging chains have a resolution on the order of 30 μm (micrometers).

22. The method according to any one of claims 16 to 19, further comprising, reconstructing, by a CT scanner control circuitry, a micro-CT image utilizing on the order of 100 projections.

* * * * *